(12) United States Patent
Labit et al.

(10) Patent No.: US 8,992,498 B2
(45) Date of Patent: Mar. 31, 2015

(54) REUSABLE DIAPERS

(76) Inventors: Jennifer Lynn Labit, Arnold, MO (US); James Andrew Labit, Arnold, MO (US)

( * ) Notice: Subject to any disclaimer, the term of this patent is extended or adjusted under 35 U.S.C. 154(b) by 263 days.

(21) Appl. No.: 13/610,161

(22) Filed: Sep. 11, 2012

(65) Prior Publication Data
US 2013/0012903 A1 Jan. 10, 2013

Related U.S. Application Data

(63) Continuation-in-part of application No. 12/059,856, filed on Mar. 31, 2008, now Pat. No. 8,262,635.

(51) Int. Cl.
| | |
|---|---|
| *A61F 13/15* | (2006.01) |
| *A61F 13/49* | (2006.01) |
| *A61F 13/493* | (2006.01) |
| *A61F 13/505* | (2006.01) |

(52) U.S. Cl.
CPC ..... *A61F 13/15268* (2013.01); *A61F 13/49004* (2013.01); *A61F 13/493* (2013.01); *A61F 13/505* (2013.01)
USPC .................................................... 604/385.15

(58) Field of Classification Search
CPC .................... A61F 13/49004; A61F 13/49003; A61F 13/491; A61F 13/493; A61F 13/539
See application file for complete search history.

(56) References Cited

U.S. PATENT DOCUMENTS

| | | | |
|---|---|---|---|
| 1,961,515 A | 6/1934 | Friedman | |
| 2,016,355 A | 10/1935 | Alsop | |
| 2,049,913 A | 8/1936 | Lesueur | |
| RE20,315 E | 3/1937 | Lesueur | |
| 2,292,030 A | 8/1942 | Kraft | |
| 2,450,059 A | 9/1948 | Rickerson | |
| 2,468,445 A | 4/1949 | Hurst | |

(Continued)

FOREIGN PATENT DOCUMENTS

| | | |
|---|---|---|
| AU | 5039493 | 1/1994 |
| BR | 03606/71 | 12/1971 |

(Continued)

OTHER PUBLICATIONS

Canadian Office Action dated Mar. 25, 2014 for Canadian application No. 2,844,249 which names the same inventors but is not related through a priority claim; 3 pages.

(Continued)

*Primary Examiner* — Susan Su
(74) *Attorney, Agent, or Firm* — Harness, Dickey & Pierce, P.L.C.

(57) ABSTRACT

A reusable diaper may include at least one fluid-absorbing insert or layer coupled to one or more inner portions of the diaper for use in absorbing fluids. The fluid-absorbing insert may be adjustable for accommodating use by a male and/or a female. In an exemplary embodiment, the fluid-absorbing insert has a first end portion and a second end portion opposite the first end portion. The first end portion is fastened to the diaper at a first location adjacent the forward waist portion. The second end portion is fastened to the diaper at a second location adjacent the rearward waist portion. The fluid-absorbing insert includes a portion between the first and second end portions that is adjustable relative to the crotch portion between the first and second locations for selectively changing an overlapped region of the at least one fluid-absorbing insert to accommodate use by a male and/or a female.

21 Claims, 10 Drawing Sheets

(56) References Cited

U.S. PATENT DOCUMENTS

| | | | |
|---|---|---|---|
| 2,493,492 A | 1/1950 | Malamut |
| 2,523,079 A | 9/1950 | Walter et al. |
| 2,532,029 A | 11/1950 | Medoff |
| 2,545,216 A | 3/1951 | Toussie |
| 2,568,590 A | 9/1951 | Laser |
| 2,575,164 A | 11/1951 | Donovan |
| 2,577,398 A | 12/1951 | Blake |
| 2,581,904 A | 1/1952 | Burns |
| 2,591,079 A | 4/1952 | Leaton |
| 2,607,348 A | 8/1952 | Rosenblatt |
| 2,627,859 A | 2/1953 | Hargrave |
| 2,664,895 A | 1/1954 | Shulman |
| 2,688,328 A | 9/1954 | Marcus |
| 2,703,577 A | 3/1955 | May |
| 2,733,715 A | 2/1956 | Folk |
| 2,788,786 A | 4/1957 | Dexter |
| 2,826,199 A | 3/1958 | Brandon |
| 2,853,073 A | 9/1958 | Brafman |
| 2,866,459 A | 12/1958 | Sobelson |
| 2,868,205 A | 1/1959 | Epstein |
| 2,893,393 A | 7/1959 | Pressley |
| 2,910,982 A | 11/1959 | Woodward |
| 2,985,170 A | 5/1961 | Title |
| 3,049,124 A | 8/1962 | Thompson |
| 3,141,461 A | 7/1964 | Farris |
| 3,162,196 A | 12/1964 | Salk |
| 3,341,394 A | 9/1967 | George |
| 3,485,706 A | 12/1969 | Evans |
| 3,530,859 A | 9/1970 | Helmowitz |
| 3,559,648 A | 2/1971 | Mason, Jr. |
| 3,658,064 A | 4/1972 | Pociluyko |
| 3,667,466 A | 6/1972 | Ralph |
| 3,741,212 A | 6/1973 | Schutte |
| 3,769,978 A | 11/1973 | DeNight et al. |
| 3,882,871 A | 5/1975 | Taniguchi |
| RE28,483 E | 7/1975 | Ralph |
| 3,926,189 A | 12/1975 | Taylor |
| 4,037,602 A | 7/1977 | Hawthorne |
| 4,338,939 A | 7/1982 | Daville |
| D269,907 S | 7/1983 | Tong |
| 4,414,971 A | 11/1983 | Chung et al. |
| 4,548,604 A | 10/1985 | Ellsworth |
| 4,568,342 A | 2/1986 | Davis |
| 4,573,987 A | 3/1986 | Lamb, Jr. |
| 4,643,726 A | 2/1987 | Gegelys |
| 4,671,793 A | 6/1987 | Hults et al. |
| 4,681,581 A | 7/1987 | Coates |
| 4,695,279 A | 9/1987 | Steer et al. |
| 4,704,117 A | 11/1987 | Mitchell |
| 4,773,906 A | 9/1988 | Krushel |
| 4,834,737 A | 5/1989 | Khan |
| 4,850,987 A | 7/1989 | Gilomen et al. |
| 4,892,598 A | 1/1990 | Stevens et al. |
| 4,904,251 A | 2/1990 | Igaue et al. |
| 4,906,243 A | 3/1990 | Dravland |
| 4,928,323 A | 5/1990 | Nathan |
| 4,950,263 A | 8/1990 | Lewis |
| 4,961,736 A | 10/1990 | McCloud |
| 4,981,480 A | 1/1991 | Gaudet et al. |
| 5,019,068 A | 5/1991 | Perez et al. |
| 5,069,672 A * | 12/1991 | Wippler et al. .......... 604/385.14 |
| 5,100,399 A | 3/1992 | Janson et al. |
| 5,106,382 A | 4/1992 | Henry |
| 5,108,385 A | 4/1992 | Snyder |
| 5,135,522 A | 8/1992 | Fahrenkrug et al. |
| 5,137,526 A | 8/1992 | Coates |
| 5,185,011 A | 2/1993 | Strasser |
| 5,207,662 A | 5/1993 | James |
| 5,217,447 A | 6/1993 | Gagnon |
| D339,633 S | 9/1993 | Porter |
| 5,304,162 A | 4/1994 | Kuen |
| 5,306,267 A | 4/1994 | Hahn et al. |
| 5,325,543 A | 7/1994 | Allen |
| 5,342,340 A | 8/1994 | Kichefski et al. |
| 5,360,422 A | 11/1994 | Brownlee et al. |
| D354,809 S | 1/1995 | Eskey |
| 5,399,177 A | 3/1995 | Blaney et al. |
| 5,405,342 A | 4/1995 | Roessler et al. |
| 5,409,476 A | 4/1995 | Coates |
| D362,717 S | 9/1995 | Caschette et al. |
| 5,454,799 A | 10/1995 | Lakiss-Smith et al. |
| 5,458,591 A | 10/1995 | Roessler et al. |
| 5,476,457 A | 12/1995 | Roessler et al. |
| D366,112 S | 1/1996 | Tollin et al. |
| 5,514,121 A | 5/1996 | Roe et al. |
| 5,527,300 A | 6/1996 | Sauer |
| 5,611,789 A | 3/1997 | Seth |
| 5,613,959 A | 3/1997 | Roessler et al. |
| 5,635,275 A | 6/1997 | Biagioli et al. |
| D386,582 S | 11/1997 | Levine |
| 5,695,488 A | 12/1997 | Sosalla |
| 5,706,524 A | 1/1998 | Herrin et al. |
| 5,722,127 A | 3/1998 | Coates |
| 5,725,518 A | 3/1998 | Coates |
| 5,814,037 A * | 9/1998 | Coates .......................... 604/393 |
| 5,891,122 A | 4/1999 | Coates |
| D436,400 S | 1/2001 | Kiecker |
| 6,168,583 B1 | 1/2001 | Tanji et al. |
| 6,254,583 B1 | 7/2001 | Coates |
| 6,315,764 B1 | 11/2001 | Faulks et al. |
| 6,322,552 B1 | 11/2001 | Blenke et al. |
| 6,379,343 B2 | 4/2002 | Stephenson et al. |
| 6,383,170 B1 | 5/2002 | Mishima et al. |
| 6,401,250 B1 | 6/2002 | McNabb |
| 6,402,731 B1 | 6/2002 | Suprise et al. |
| 6,423,047 B1 | 7/2002 | Webster |
| 6,471,681 B1 | 10/2002 | Ronnberg et al. |
| 6,482,194 B1 | 11/2002 | Putzer |
| 6,540,730 B1 | 4/2003 | Niedermeyer |
| 6,562,016 B2 | 5/2003 | Shinkai |
| 6,569,137 B2 | 5/2003 | Suzuki et al. |
| 6,579,273 B2 * | 6/2003 | Dupuy ...................... 604/385.14 |
| 6,616,645 B1 | 9/2003 | Moravek |
| 6,623,466 B1 | 9/2003 | Richardson |
| 6,639,041 B2 | 10/2003 | Nishikawa et al. |
| 6,641,569 B1 | 11/2003 | Coles et al. |
| 6,766,817 B2 | 7/2004 | da Silva |
| 6,767,498 B1 | 7/2004 | Talley et al. |
| 6,918,404 B2 | 7/2005 | da Silva |
| 6,989,005 B1 | 1/2006 | LaVon et al. |
| 7,066,586 B2 | 6/2006 | da Silva |
| 7,244,398 B2 | 7/2007 | Kotary et al. |
| 7,285,255 B2 | 10/2007 | Kadlec et al. |
| 7,361,803 B2 | 4/2008 | Miskie |
| 7,591,811 B2 | 9/2009 | Wilkinson |
| 7,629,501 B2 | 12/2009 | Labit et al. |
| 8,062,276 B2 | 11/2011 | Labit et al. |
| 8,262,635 B2 | 9/2012 | Labit et al. |
| 8,439,887 B1 * | 5/2013 | Magee ...................... 604/385.01 |
| 8,728,052 B2 * | 5/2014 | Wang et al. ................... 604/399 |
| 2001/0034510 A1 * | 10/2001 | Shinkai ...................... 604/385.01 |
| 2002/0010452 A1 | 1/2002 | Dupuy |
| 2002/0045876 A1 * | 4/2002 | Suzuki et al. ............. 604/385.28 |
| 2002/0094740 A1 | 7/2002 | Li et al. |
| 2003/0014024 A1 | 1/2003 | Kiecker |
| 2003/0083635 A1 | 5/2003 | Gibbs |
| 2003/0109841 A1 | 6/2003 | Edwards |
| 2004/0002691 A1 * | 1/2004 | Popp et al. .................... 604/387 |
| 2004/0044323 A1 | 3/2004 | Roessler et al. |
| 2004/0082933 A1 | 4/2004 | Karami |
| 2004/0210206 A1 * | 10/2004 | Coates ............................ 604/386 |
| 2004/0236298 A1 | 11/2004 | Coates |
| 2004/0236300 A1 | 11/2004 | Gibbs et al. |
| 2004/0267219 A1 | 12/2004 | Olmedo |
| 2005/0085784 A1 | 4/2005 | LeMinh et al. |
| 2005/0148258 A1 | 7/2005 | Chakravarty et al. |
| 2005/0210560 A1 | 9/2005 | Coates |
| 2005/0228356 A1 | 10/2005 | LaVon et al. |
| 2005/0228357 A1 * | 10/2005 | Mishima et al. ......... 604/385.19 |
| 2006/0100597 A1 * | 5/2006 | Miskie ........................... 604/378 |
| 2006/0167432 A1 | 7/2006 | Sigari |
| 2007/0066952 A1 | 3/2007 | LaVon et al. |
| 2008/0015531 A1 | 1/2008 | Hird et al. |
| 2008/0065039 A1 | 3/2008 | Labit et al. |

(56) References Cited

U.S. PATENT DOCUMENTS

| | | | |
|---|---|---|---|
| 2008/0215027 A1 | 9/2008 | Labit et al. | |
| 2009/0216209 A1* | 8/2009 | Ekstrom | 604/367 |
| 2009/0299313 A1* | 12/2009 | Knightingale et al. | 604/367 |
| 2010/0036340 A1 | 2/2010 | Allison-Rogers | |
| 2010/0036353 A1* | 2/2010 | Payne | 604/385.08 |
| 2010/0087794 A1 | 4/2010 | Labit et al. | |
| 2010/0108554 A1 | 5/2010 | Melius et al. | |
| 2010/0168709 A1* | 7/2010 | Hodgkin | 604/385.14 |
| 2010/0280477 A1* | 11/2010 | Henderson et al. | 604/385.15 |
| 2011/0137278 A1 | 6/2011 | Ormsby et al. | |
| 2011/0319852 A1 | 12/2011 | Labit | |
| 2012/0010585 A1 | 1/2012 | Labit et al. | |
| 2012/0016333 A1 | 1/2012 | Labit et al. | |
| 2012/0123364 A1* | 5/2012 | Coates | 604/360 |
| 2012/0172827 A1* | 7/2012 | Dupuy | 604/378 |
| 2013/0053805 A1* | 2/2013 | Catoe | 604/367 |
| 2013/0158499 A1* | 6/2013 | Thompson | 604/385.14 |
| 2013/0190712 A1* | 7/2013 | Vaughan | 604/385.14 |
| 2013/0237940 A1* | 9/2013 | Wang et al. | 604/370 |
| 2014/0081232 A1* | 3/2014 | Ormsby | 604/385.03 |
| 2014/0296820 A1* | 10/2014 | Malone | 604/385.201 |

FOREIGN PATENT DOCUMENTS

| | | |
|---|---|---|
| BR | 360571 | 12/1971 |
| CA | 2097437 | 12/1993 |
| CA | 2103537 | 2/1995 |
| DE | 4326271 | 2/1995 |
| EP | 0099846 | 2/1984 |
| EP | 0486006 | 11/1991 |
| EP | 0475702 | 3/1992 |
| EP | 2106775 | 10/2009 |
| ES | 2115559 | 6/1998 |
| GB | 493819 | 10/1938 |
| GB | 0849573 | 9/1960 |
| GB | 0803716.0 | 2/2008 |
| JP | 04150853 | 5/1992 |
| JP | 08000662 | 1/1996 |
| WO | WO-8705471 | 9/1987 |
| WO | WO-9007313 | 7/1990 |
| WO | WO-9403137 | 2/1994 |
| WO | WO-94/15563 | 7/1994 |
| WO | WO-95/23569 | 9/1995 |
| WO | WO-9824388 | 6/1998 |
| WO | WO 9933421 | 7/1999 |
| WO | WO-2008030984 | 3/2008 |
| WO | WO-2008/142634 | 11/2008 |
| WO | WO 2009/106899 | 9/2009 |
| ZA | 8701842 | 11/1988 |

OTHER PUBLICATIONS

Derwent abstract and Figure of CA 2024375 A, publication date Mar. 1, 1992.
Definition of "waterproof", Webster's Third New International Dictionary, unabridged, 1993.
http://www.wonderworksbabyco.com/products.htm, 5 pages, accessed and printed Sep. 8, 2006.
http://fuzzibunz.com/Fuzzi-Bunz-Colors.htm, 2 pages, accessed and printed Sep. 8, 2006.
http://www.tinytush.com/6 pages, accessed and printed Sep. 8, 2006.
http://web.archive.org/web/20041010045134/www.changingbabies.com/anatomyof-adiaper.html; accessed Apr. 27, 2007, 17 pages.
http://www.aplix.com/en/layout/set/print/content/search, accessed Apr. 27, 2007, 3 pages.
http://www.cottonbabies.com/index.php, 7 pages, accessed on Aug. 24, 2006.
http://www.diapersite.com/baby.sub.--diapers.sub.--specs.htm, 4 pages, accessed Apr. 23, 2008.
http://www.diapersite.com/images/diaperspecs/velcro.htm, 1 page, accessed Apr. 23, 2008.
http://tubarc.blogspot.com/, 206 pages, accessed Sep. 15, 2008.
http://hydrology-tubarc.blogspot.com/ 32 pages, accessed Sep. 15, 2008.
http://ip-know-how-tubarc.blogspot.com/, 8 pages, accessed Sep. 15, 2008.
Derwent Abstract and Figure of AU 9539089 A, published Jun. 27, 1996.
FuzziBunz, A better diaper for a better planet, Newsletter, FuzziBunz Press Releases, 5 pages, (Jul. 10, 2007).
Restriction Requirement dated Aug. 17, 2010, issued in Design U.S. Appl. No. 29/305,970, which includes an inventor in common with the instant application; 7 pages.
Office Action dated Dec. 21, 2010 issued in Design U.S. Appl. No. 29/305,970, which includes an inventor in common with the instant application; 7 pages.
Final Office Action dated Jun. 23, 2011 issued in Design U.S. Appl. No. 29/305,970, which includes an inventor in common with the instant application; 6 pages.
Office Action dated Dec. 22, 2010 issued in Design U.S. Appl. No. 29/376,135, which includes an inventor in common with the instant application; 7 pages.
Final Office Action dated Jun. 22, 2011 issued in Design U.S. Appl. No. 29/376,135, which includes an inventor in common with the instant application; 6 pages.
Office Action dated Dec. 22, 2010 issued in Design U.S. Appl. No. 29/376,138, which includes an inventor in common with the instant application; 8 pages.
Final Office Action dated Jun. 22, 2011 issued in Design U.S. Appl. No. 29/376,138, which includes an inventor in common with the instant application; 6 pages.
Office Action dated Dec. 21, 2010 issued in Design U.S. Appl. No. 29/376,139, which includes an inventor in common with the instant application; 7 pages.
Final Office Action dated Jun. 22, 2011 issued in Design U.S. Appl. No. 29/376,139, which includes an inventor in common with the instant application; 6 pages.
Office Action dated Jul. 28, 2010 issued in European Application No. 09156960.8 (now published as EP2106775), which also claims priority to the same U.S. Appl. No. 12/059,856 (now issued as 8,262,635) as the instant application; 1 page.
International Search Report and Written Opinion dated Oct. 29, 2009, issued in International Patent Application No. PCT/US2009/0038830 (now published as WO 2009/146021) which also claims priority to the same U.S. Appl. No. 12/059,856 (now issued as 8,262,635) as the instant application; 11 pages.
Extended European Search Report dated Jul. 3, 2009 issued in European Application No. 09156960.8 (now published as EP2106775), which also claims priority to the same U.S. Appl. No. 12/059,856 (now issued as 8,262,635) as the instant application; 7 pages.
International Search Report and Written Opinion dated Apr. 3, 2008, issued in International Patent Application No. PCT/US07/77788 (now published as WO 2008/030984) which names the same inventors as the instant application but is not related through a priority claim; 12 pages.
US Patent Office Non-final Office action dated Jun. 6, 2012 issued in U.S. Appl. No. 12/632,315, which includes an inventor in common with the instant application; 28 pgs.
US Patent Office Final Office action dated Jan. 9, 2013 issued in U.S. Appl. No. 12/632,315, which includes an inventor in common with the instant application; 14 pgs.
US Patent Office Final Office action dated Jul. 16, 2013 issued in U.S. Appl. No. 12/632,315, which includes an inventor in common with the instant application; 14 pgs.

* cited by examiner

REUSABLE DIAPERS

CROSS-REFERENCE TO RELATED APPLICATION

This application is a continuation-in-part of U.S. patent application Ser. No. 12/059,856 filed Mar. 31, 2008, which issued as U.S. Pat. No. 8,262,635 on Sep. 11, 2012. The entire disclosure of the above application is incorporated herein by reference.

FIELD

The present disclosure relates generally to reusable diapers.

BACKGROUND

The statements in this background section merely provide background information related to the present disclosure and may not constitute prior art.

Absorbent articles, such as disposable diapers, training pants, or incontinence pads, generally have an absorbent core intended for single use only. Once the absorbent core component is saturated with bodily discharges, such as urine, the entire absorbent article is usually discarded. Oftentimes, parts of a disposable diaper or training pants could be reused. But with the unitary construction, they are nevertheless discarded along with the saturated absorbent cores. In addition to the added cost and waste associated with discarding such products, it is often inconvenient to acquire and store quantities of such disposable absorbent articles.

SUMMARY

According to various aspects, exemplary embodiments are provided of reusable diapers. In an exemplary embodiment, a gender neutral reusable diaper generally includes at least one fluid-absorbing insert or layer coupled to one or more inner portions of the diaper for use in absorbing fluids. The fluid-absorbing insert may be adjustable for accommodating use by a male and/or a female. In an exemplary embodiment, the fluid-absorbing insert has a first end portion and a second end portion opposite the first end portion. The first end portion is fastened to the diaper at a first location adjacent the forward waist portion. The second end portion is fastened to the diaper at a second location adjacent the rearward waist portion. The fluid-absorbing insert includes a portion between the first and second end portions that is adjustable relative to the crotch portion between the first and second locations for selectively changing an overlapped region of the at least one fluid-absorbing insert to accommodate use by a male and/or a female.

Further aspects and features of the present disclosure will become apparent from the detailed description provided hereinafter. In addition, any one or more aspects of the present disclosure may be implemented individually or in any combination with any one or more of the other aspects of the present disclosure. It should be understood that the detailed description and specific examples, while indicating exemplary embodiments of the present disclosure, are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
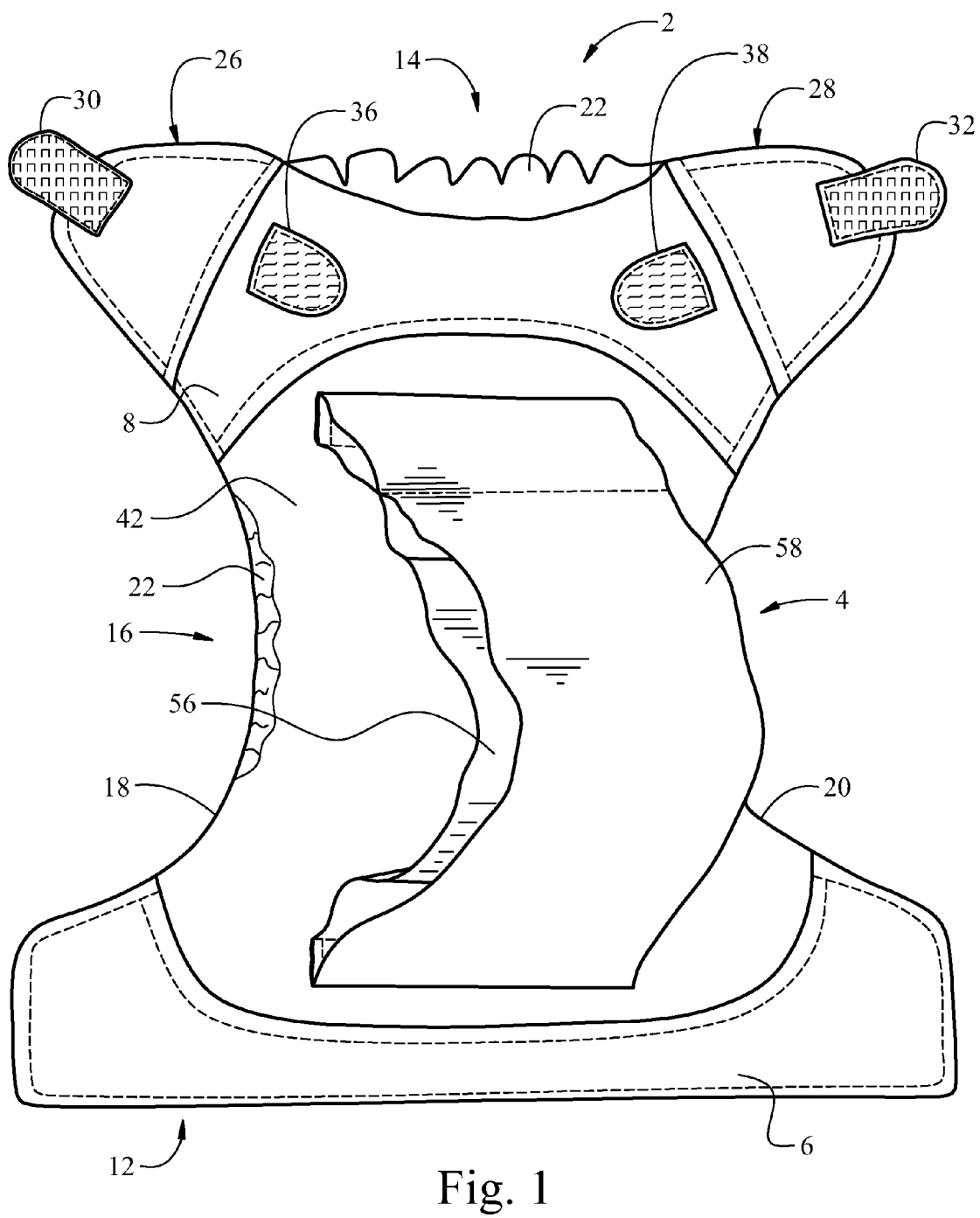
FIG. 1 is an inner perspective view of an exemplary embodiment of a gender neutral reusable diaper having an adjustable fluid-absorbing insert for use in absorbing fluids within the reusable diaper.

The following description is merely exemplary in nature and is not intended to limit the present disclosure, application, or uses. It should be understood that throughout the drawings, corresponding reference numerals indicate like or corresponding parts and features.

Referring now to the drawings, FIGS. 1-5 illustrate an exemplary embodiment of an adjustable, gender neutral reusable diaper 2 embodying one or more aspects of the present disclosure. As will be described, the exemplary reusable diaper 2 may be adjusted as desired to accommodate use by a male and/or a female wearer. More particularly, at least one fluid-absorbing insert, pad, or layer 4 of the reusable diaper 2 may be adjusted as desired to accommodate use by the male and/or female wearer. As will also be described, the reusable diaper 2 may also be adjusted (e.g., via adjustment system 46, etc.) to fit different sized male and/or female wearers, and/or may include liquid-resistant regions 6, 8 located to help resist undesired movement of moisture through the reusable diaper 2 (e.g., through forward and rearward waist portions 12, 14, etc.).

Figure 2:
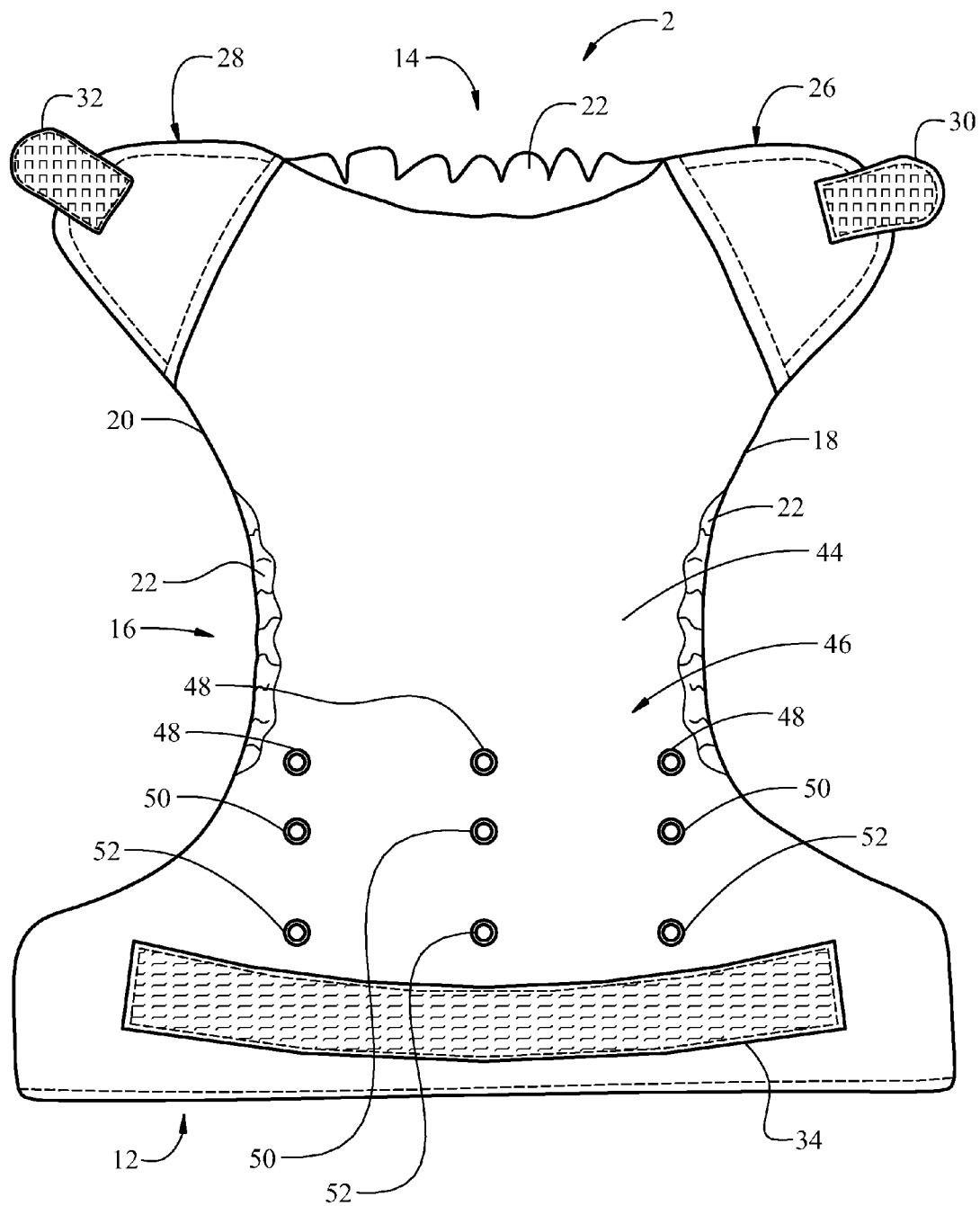
FIG. 2 is an outer view of the reusable diaper shown in FIG. 1.
Figure 3:
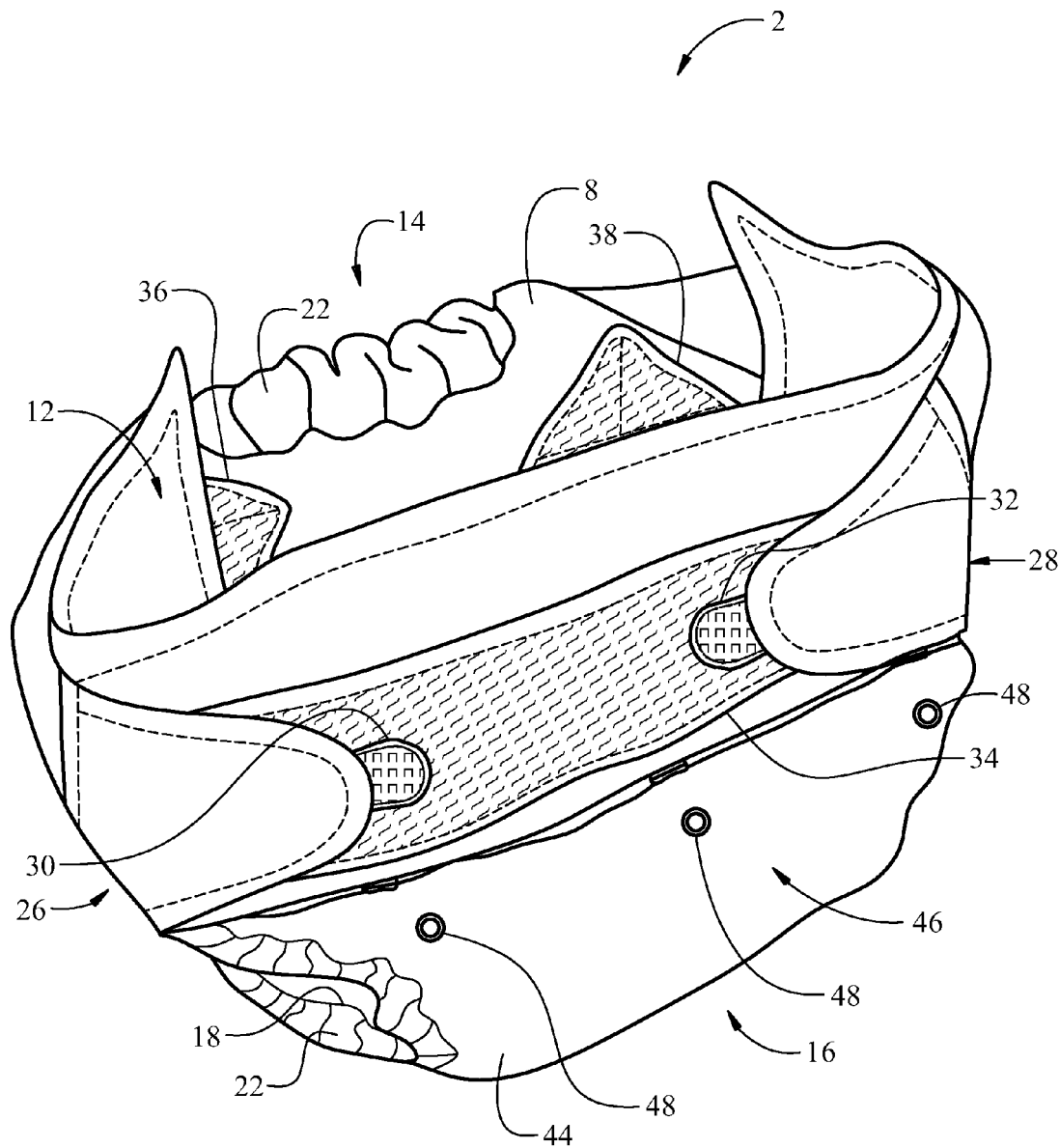
FIG. 3 is a perspective view of the reusable diaper of FIG. 1 shown secured in a generally closed position.

With reference to FIGS. 1-3, the reusable diaper 2 generally includes a forward waist portion 12, a rearward waist portion 14, and a crotch portion 16 disposed generally between the forward and rearward waist portions 12, 14. The contours of the forward and rearward waist portions 12, 14, together with the crotch portion 16, cooperatively define leg openings 18, 20 generally within the crotch portion 16 to accommodate a wearer's legs. In the illustrated embodiment, the leg openings 18, 20 include elastic 22 disposed adjacent the periphery of the leg openings 18, 20 for example, to help draw and hold the reusable diaper 2 securely against the wearer's legs, to inhibit leaking of fluids out of the reusable diaper 2 through the leg openings 18, 20, etc.

The rearward waist portion 14 of the reusable diaper 2 includes corner regions 26, 28 that may be releasably attached to the forward waist portion 12 to secure the reusable diaper 2 in a desired position (e.g., in a generally closed position as shown in FIG. 3, etc.). More particularly, tabs 30, 32 of the respective corner regions 26, 28 may be releasably attached (e.g., via corresponding hook-and-loop fasteners, etc.) to an elongate strip 34 of the forward waist portion 12 to secure the diaper 2 in the desired position (e.g., in the generally closed position, etc.). Elastic 22 is disposed along the rearward waist portion 14 to help ensure a snug fit of the reusable diaper 2 around a wearer's waist.

The tabs 30, 32 of the reusable diaper's corner regions 26, 28 may also be releasably attached to each other, for example, for closing the diaper 2 for storage, etc. For example, one of the tabs 30, 32 may have a forward surface with hook-and-loop fasteners that are releasably attachable to corresponding hook-and-loop fasteners on a rearward surface of the other tab 30, 32. The tabs 30, 32 may also be releasably attached to interior laundry closures 36, 38 of the rearward waist portion 14 (e.g., via corresponding hook-and-loop fasteners, etc.). This may, for example, help prevent or at least reduce snagging of the tabs 30, 32 when the reusable diaper 2 is being washed or laundered.

The corner regions 26, 28 and/or the tabs 30, 32 of the reusable diaper 2 may also be resiliently stretchable. This may allow for at least some adjustability of the diaper's functional waist size as defined by the forward and rearward waist portions 12, 14 when the rearward waist portion 14 is releasably attached to the forward waist portion 12 (e.g., via tabs 30, 32, etc.) in the generally closed position. For example, the corner regions 26, 28 may be formed from about 95% polyester and about 5% Lycra to allow them to stretch. However, the corner regions 26, 28 may be formed from other suitable materials within the scope of the present disclosure, and may or may not be resiliently stretchable.

Having resiliently elastic or stretchable corner regions 26, 28 (and/or tabs 30, 32 and/or elastic 22) with the ability to stretch can allow for tailoring of the diaper's functional waist size to the wearer's actual waist size. For example, the diaper's functional waist size may be selectively tailored for the wearer by stretching the corner regions 26, 28 (and/or tabs 30, 32 and/or elastic 22), and then releasably attaching the tabs 30, 32 to the elongate strip 34 at desired attachment locations along the length of the elongate strip 34. In this exemplary manner, the diaper's functional waist size can be selectively adjusted, for example, to provide a relatively snug fit about the waist of the wearer (e.g., infant, toddler, adult, etc.), and preferably without being too uncomfortably tight about the wearer's thighs.

While the tabs 30, 32, the elongate strip 34, and the laundry closures 36, 38 of the reusable diaper 2 are each disclosed as including corresponding hook-and-loop fasteners, other suitable fasteners for coupling corresponding portions of the reusable diaper 2 together may be used within the scope of the present disclosure. For example, tabs, elongate strips, and/or laundry closures may include one or more of different hook-and-loop fastener arrangements (e.g., two or more spaced-apart discrete patches along the second waist portion instead of a single elongate strip, etc.), adhesives, snaps, buttons, clasps, various hook and loop closures, magnets, combinations thereof, etc. within the scope of the present disclosure.

With continued reference to FIGS. 1-3, the illustrated reusable diaper 2 also generally includes an inner layer 42 (FIG. 1) and an outer layer 44 (FIGS. 2 and 3) generally coupled to the inner layer 42 (e.g., seamed, stitched, melted, etc.). The inner layer 42 and the outer layer 44 may broadly be viewed as defining at least part of the forward and rearward waist portions 12, 14, and at least part of the crotch portion 16 of the reusable diaper 2. The inner layer 42 may be configured to absorb, wick, etc. moisture generally away, for example, from a diaper wearer, and may be formed of, for example, organic cotton, any suitable absorbent material, etc. The outer layer or shell 44 may be configured to be substantially liquid-impervious to thereby resist wicking of moisture through the outer layer 44, and may be formed of polyester, water resistant material, coated materials, laminated materials, etc.

With particular reference to FIG. 1, the inner layer 42 includes two liquid-resistant regions 6, 8 that, for example, help resist wicking, movement, etc. of moisture through the inner layer 42 past the liquid-resistant regions 6, 8. A forward liquid-resistant region 6 is disposed adjacent the forward waist portion 12. A rearward liquid-resistant region 8 is disposed adjacent the rearward waist portion 14. The forward and rearward liquid-resistant regions 6, 8 each generally include a strip of material that may be coupled (e.g., seamed, stitched, melted, etc.), for example, to the inner layer 42 and/or to the outer layer 44. Each liquid-resistant region 6, 8 extends generally across a width of the reusable diaper's inner layer 42 to resist wicking, movement, etc. of moisture substantially along the width of the inner layer 42. As such, the forward liquid-resistant region 6 may be viewed as defining at least part of the forward waist portion 12, and the rearward liquid-resistant region 8 may be viewed as defining at least part of the rearward waist portion 14. It should be appreciated that a wide range of suitable materials, coatings, etc. may be used for the liquid-resistant regions 6, 8, including, for example, polyester materials, durable water repellant coatings, laminated fabrics, coated fabrics, etc.

As stated above, the two liquid-resistant regions 6, 8 of the illustrated reusable diaper 2 may help resist wicking, movement, etc. of moisture through the diaper 2 past the liquid-resistant regions 6, 8. In the illustrated embodiment, for example, the forward and rearward liquid-resistant regions 6, 8 are generally disposed adjacent the respective forward and rearward waist portions 12, 14, generally between the waist portions 12, 14 and the fluid-absorbing insert 4. This positioning may help resist wicking, movement, etc. of fluid from the fluid-absorbing insert 4, the inner layer 42, etc., through the forward and/or rearward waist portions 12 and/or 14 and to a shirt, blanket, article of bedding, etc. that may come into contact with the respective forward and/or rearward waist portions 12 and/or 14 (e.g., with an inner part of the forward and/or rearward waist portions 12 and/or 14, etc.). In other exemplary embodiments, reusable diapers may include inner layers having liquid-resistant regions shaped differently than disclosed herein; having liquid-resistant regions disposed, located, etc. differently than disclosed herein; having liquid-resistant regions with one or more separated parts; having less than or more than two liquid-resistant regions; etc. For example, in one exemplary embodiment, one or more liquid-resistant regions may be disposed adjacent one or more of a forward waist portion, a rearward waist portion, leg regions, etc. of a reusable diaper.

With particular reference now to FIGS. 2 and 3, an adjustment system 46 is provided along the outer layer 44 of the reusable diaper 2 adjacent the forward waist portion 12 to allow for customization or adjustment to the reusable diaper's functional rise and/or crotch length. For example, the adjustment system 46 may allow for adjustment of the reusable diaper 2 such that the reusable diaper 2 may be adjusted to fit different sized wearers. This feature, in combination with the resiliently elastic or stretchable corner regions 26, 28 (and/or tabs 30, 32), elastic 22, etc.), may provide a generally one-size-fits all reusable diaper 2. This feature may also help create an even better and/or snugger fit to the diaper wearer (e.g., in combination with the resiliently elastic or stretchable corner regions 26, 28 (and/or tabs 30, 32), elastic 22, etc.). For example, the adjustment system 46 may help reduce the extent to which the crotch portion 16 hangs down below the wearer, and the corner region 26, 28 (and/or tabs 30, 32) and/or elastic 22 may help securely hold the reusable diaper 2 around a wearer's waist and/or legs. Adjustment systems may be located differently than disclosed herein (e.g., adjacent rearward waist portions, adjacent crotch portions, etc.) within the scope of the present disclosure.

The illustrated adjustment system 46 includes a three-by-three array of snaps 48, 50, 52, horizontally arranged and aligned in three rows and vertically arranged and aligned in three columns. A first row includes three spaced-apart female snaps 48; a second, or middle, row includes three spaced-apart female snaps 50; and a third row includes three-spaced apart male snaps 52. The first row of snap members 48 is vertically spaced from and aligned with the corresponding snap members 50, 52 in the two other rows of the array. Each row of snap members includes a first snap member located generally centrally across a width of the diaper 2, a second snap member located toward one lateral side of the diaper 2, and a third snap member located toward another lateral side of the diaper 2.

The male snaps 52 can be snapped together with either the female snaps 48 of the first row, or the female snaps 50 of the second row. For example, as shown in FIG. 3, the male snaps 52 of the third row can be snapped together with the corresponding female snaps 50 of the second row to thereby decrease the diaper's functional rise and/or crotch length. To decrease the diaper's functional rise and/or crotch length to an even greater extent, the male snaps 52 of the third row may instead be snapped together with the corresponding female snaps 48 of the first row.

The illustrated array of snaps 48, 50, 52 thus provide three different sizing configurations for the reusable diaper 2. The functional rise and/or crotch length of the reusable diaper 2 may be changed by selectively choosing whether to engage the male snaps 52 with the female snaps 48 of the first row, with the female snaps 50 of the second row, or by simply choosing to do neither. Thus, the exemplary three-by-three arrangement can eliminate or at least reduce the bulge in the middle front of the diaper 2 that typically occurs when there are only two columns of snaps due to the fabric bulging out between the two snaps. The three-by-three snap arrangement may help enable the diaper 102 to be more of a one-size fits all diaper 2.

The snaps 48, 50, 52 of the illustrated adjustment system 46 may be formed from a plastic material. Alternatively, the snaps 48, 50, 52 may be formed from other materials, for example lightweight and durable materials that can withstand repeated laundry cycles. In other exemplary embodiments, reusable diapers may include more or less than nine snaps and/or snaps arranged differently than illustrated herein. In addition, reusable diapers may include snaps in other arrangements than disclosed herein, for example, two rows of male snaps with only one row of female snaps, or rows having both male and female snaps. Additional exemplary embodiments include reusable diapers with more or less than three rows of snap members and/or more or less than three columns of snap members.

While the illustrated adjustment system 46 includes an array of snaps 48, 50, 52, other exemplary adjustment systems may be used within the scope of the present disclosure. For example, adjustment systems may include adhesives, buttons, clasps, various hook and loop closures, magnets, elastic straps, adjustable straps, combinations thereof, etc.

Figure 4:
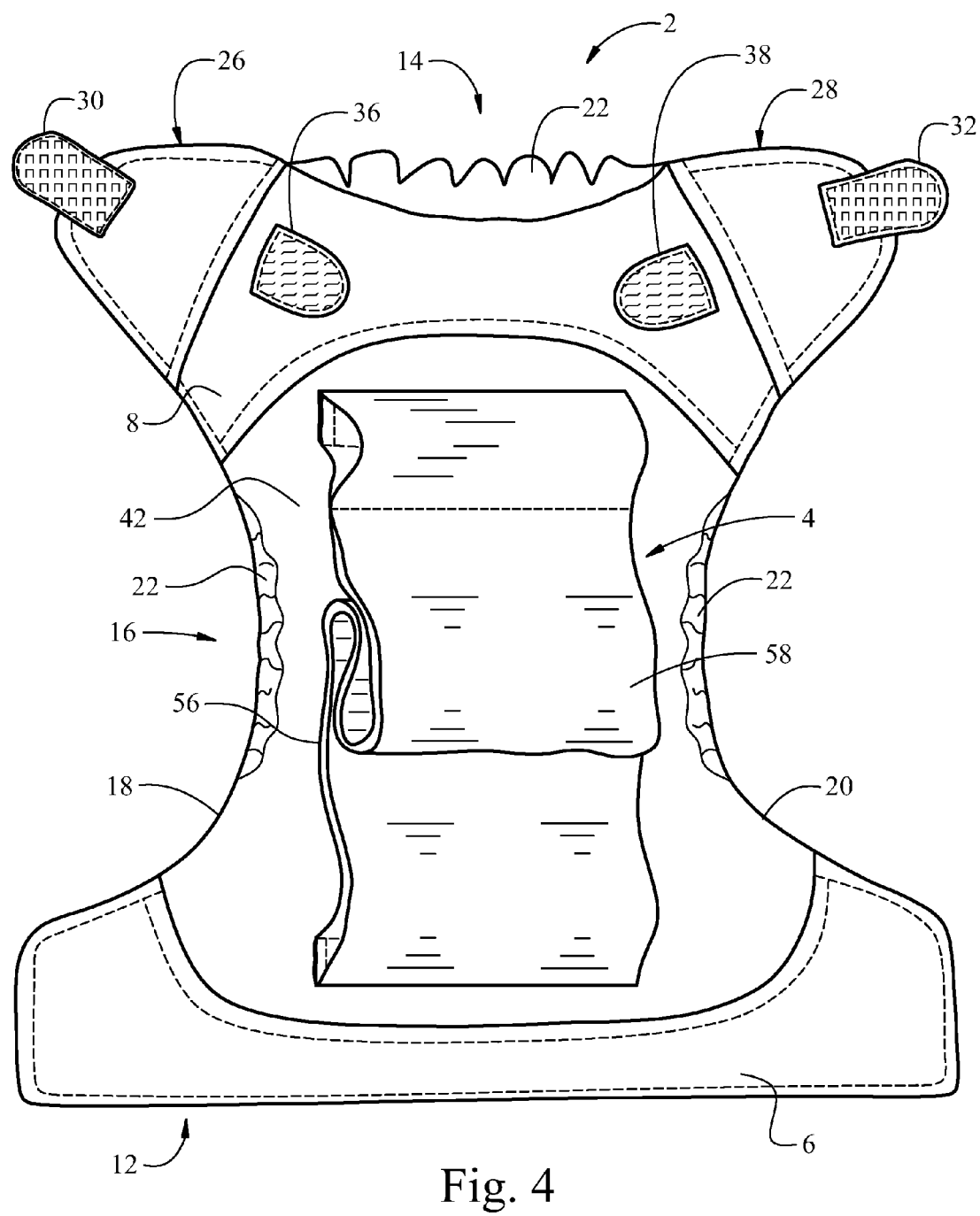
FIG. 4 is a view similar to FIG. 1 with the fluid-absorbing insert shown at least partly folded over itself in position for accommodating use by a female wearer.
Figure 5:
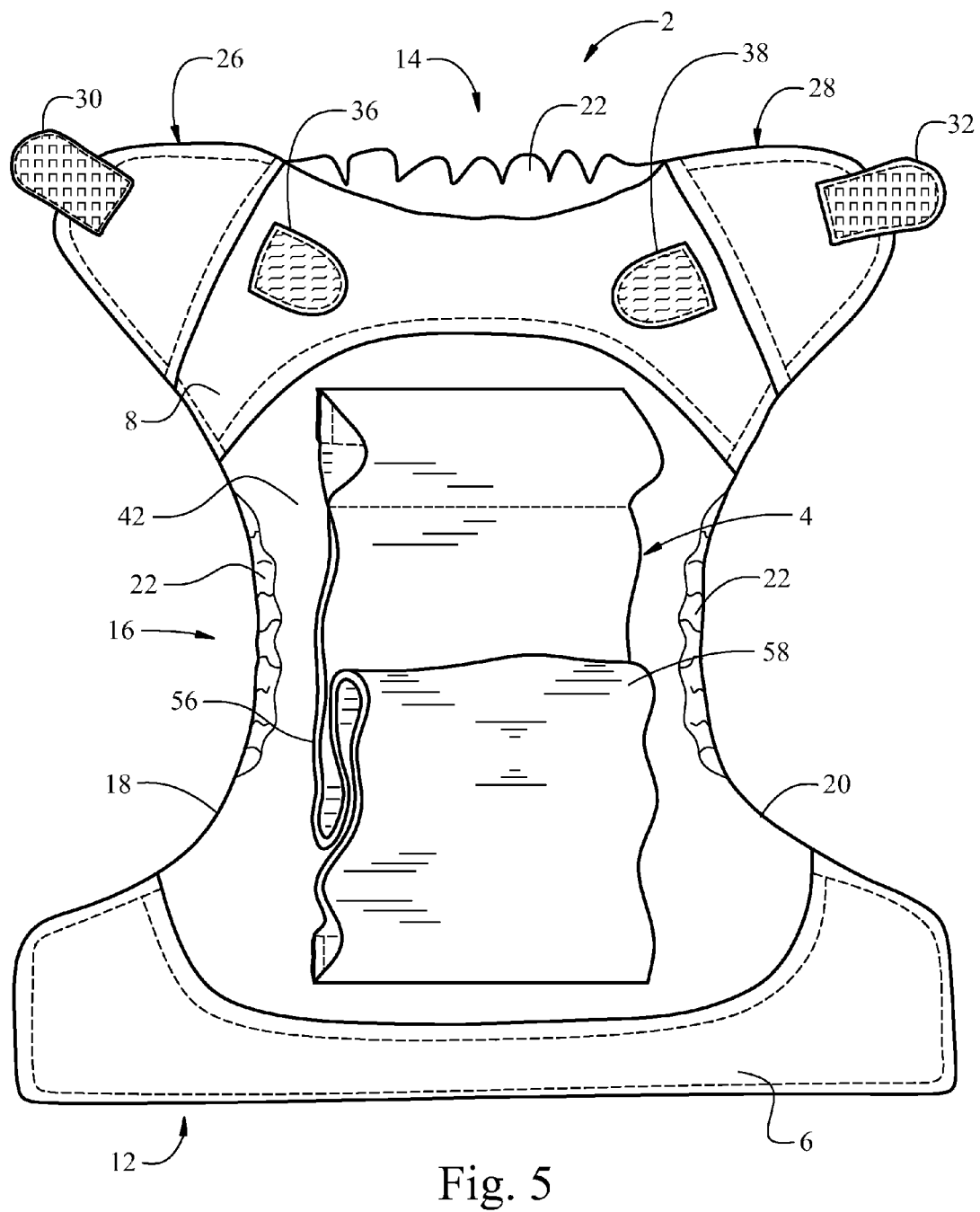
FIG. 5 is a view similar to FIG. 1 with the fluid-absorbing insert shown at least partly folded over itself in position for accommodating use by a male wearer.

With reference now to FIGS. 1, 4, and 5, the adjustable fluid-absorbing insert 4 of the reusable diaper 2 will be described. The fluid-absorbing insert 4 is positioned within the reusable diaper 2 to absorb liquids within the reusable diaper 2, for example liquids discharged into the reusable diaper 2 by a wearer, etc. In the illustrated embodiment, the fluid-absorbing insert 4 is coupled to the reusable diaper's inner layer 42 such that the inner layer 42 is disposed generally between the outer layer 44 and the fluid-absorbing insert 4. In this position, the fluid-absorbing insert 4 may absorb liquids within the reusable diaper 2 (e.g., fluids discharged by the diaper's wearer), and the inner layer 42 may absorb liquids within the reusable diaper 2 that, for example, move outwardly past the fluid-absorbing insert 4, soak through the fluid-absorbing insert 4, etc.

As best shown in FIG. 1, the illustrated fluid-absorbing insert 4 includes two individual and separate (and at least partly spaced apart) layers 56, 58 of material. The two layers 56, 58 are each stitched to the reusable diaper's inner layer 42 at two locations: a first location adjacent the forward waist portion 12 and a second location adjacent the rearward waist portion 14. For example, free ends of each of the layers 56, 58 may be overlapped and then stitched to the inner layer 42. The two layers 56, 58 may further be stitched together at a third location adjacent the rearward waist portion 14. This may help hold the two layers 56, 58 in position together, and/or may help with sizing and positioning the two layers 56, 58 as desired. In other exemplary embodiments, reusable diapers may include fluid-absorbing inserts having more than or less than two layers of material. In addition, fluid-absorbing insert layers may be coupled together differently and/or may be coupled to reusable diapers differently (e.g., to inner layers of the reusable diapers at locations other than disclosed herein (e.g., adjacent crotch portions, etc.)) within the scope of the present disclosure. Moreover, a single piece of material may be used to form fluid-absorbing insert layers.

The layers 56, 58 of the illustrated fluid-absorbing insert 4 are formed from organic cotton material. But the fluid-absorbing insert layers 56, 58 may comprise in part or in whole one or more of microfibers, hemp, hydrocolloid materials, other suitable absorbent materials, combinations thereof, etc. within the scope of the present disclosure. Materials other than organic materials may also be used.

As shown in FIGS. 4 and 5, the layers 56, 58 of the fluid-absorbing insert 4 are together adjustable relative to the reusable diaper's inner layer 42, for example, for accommodating use of the reusable diaper 2 either by a female wearer (e.g., FIG. 4, etc.) or a male wearer (e.g., FIG. 5, etc.). The fluid-absorbing insert layers 56, 58 are thus also viewed as adjustable relative to the reusable diaper's forward waist portion 12 and rearward waist portion 14, at locations generally between the forward waist portion 12 and rearward waist portion 14. Such adjustability may allow for positioning the layers 56, 58 of the fluid-absorbing insert 4 as desired to ensure that fluids, for example fluids discharged into the reusable diaper 2 by a wearer, are substantially absorbed by the fluid-absorbing insert 4. Thus, this may help inhibit fluids from pooling and/or leaking out of the reusable diaper 2 onto the wearer's clothes, body, bedding, toys, furniture, etc.

To adjust the fluid-absorbing insert 4, the layers 56, 58 are folded, bulked up, gathered, etc. over themselves to provide an overlapped, layered, built up, etc. region at the desired location (e.g., at the desired location to accommodate the female or male wearer, etc.). This overlapped region may provide additional liquid absorbing capacity (e.g., additional absorbing material, layers, etc.) at the desired location within the reusable diaper 2, and thus help inhibit undesired leaks. As shown in FIG. 4, for example, the fluid-absorbing insert layers 56, 58 can be folded over themselves adjacent the reusable diaper's crotch portion 16 to accommodate use by a female wearer. Here, the fluid-absorbing insert layers are overlapped at a typical central location to absorb fluids discharged by the female wearer. And as shown in FIG. 5, for example, the fluid-absorbing insert layers 56, 58 can be folded over themselves adjacent the reusable diaper's forward waist portion 12 to accommodate use by a male wearer. Here, the fluid-absorbing insert layers 56, 58 are overlapped at a typical forward location to absorb fluids discharged by the male wearer.

It should now be appreciated that the reusable diaper 2 may be put on either male or female wearers having varying, differing, etc. body sizes, waist sizes, etc. The adjustment system may first be adjusted to accommodate the body size of the wearer. The reusable diaper may then be put on the wearer with the fluid-absorbing insert 4 (as well as part of the inner layer 42) positioned against the skin of the wearer. The fluid-absorbing insert 4 may be folded, bulked up, etc. at the desired location to accommodate a male or female wearer. The first and second corner regions 26, 28 (e.g., the tabs 30, 32) of the rearward waist portion 14 may next be secured to the elongate strip 34 of the forward waist portion 12 to secure the reusable diaper 2 on the wearer. In this position, the fluid-absorbing insert 4 and/or the inner layer 42 can absorb moisture from the wearer (e.g., bodily discharge, urine, sweat, etc.). When the fluid-absorbing insert 4 becomes saturated, the reusable diaper 2 may be removed from the wearer and washed or laundered. After the reusable diaper 2 (and fluid-absorbing insert 4) has been satisfactorily washed and dried, the reusable diaper 2 may be reused.

FIGS. 6-10 illustrate another exemplary embodiment of an adjustable, gender neutral reusable diaper 102 embodying one or more aspects of the present disclosure. As will be described, the exemplary reusable diaper 102 may be adjusted as desired to accommodate use by a male and/or a female wearer. More particularly, at least one fluid-absorbing insert, pad, or layer 104 of the reusable diaper 102 may be adjusted as desired to accommodate use by the male and/or female wearer. As will also be described, the reusable diaper 102 may also be adjusted (e.g., via adjustment system 146 (FIG. 7), etc.) to fit different sized male and/or female wearers, and/or may include liquid-resistant regions 106, 108 (FIG. 6) located to help resist undesired movement of moisture through the reusable diaper 102 (e.g., through forward and rearward waist portions 112, 114, etc.).

Figure 6:
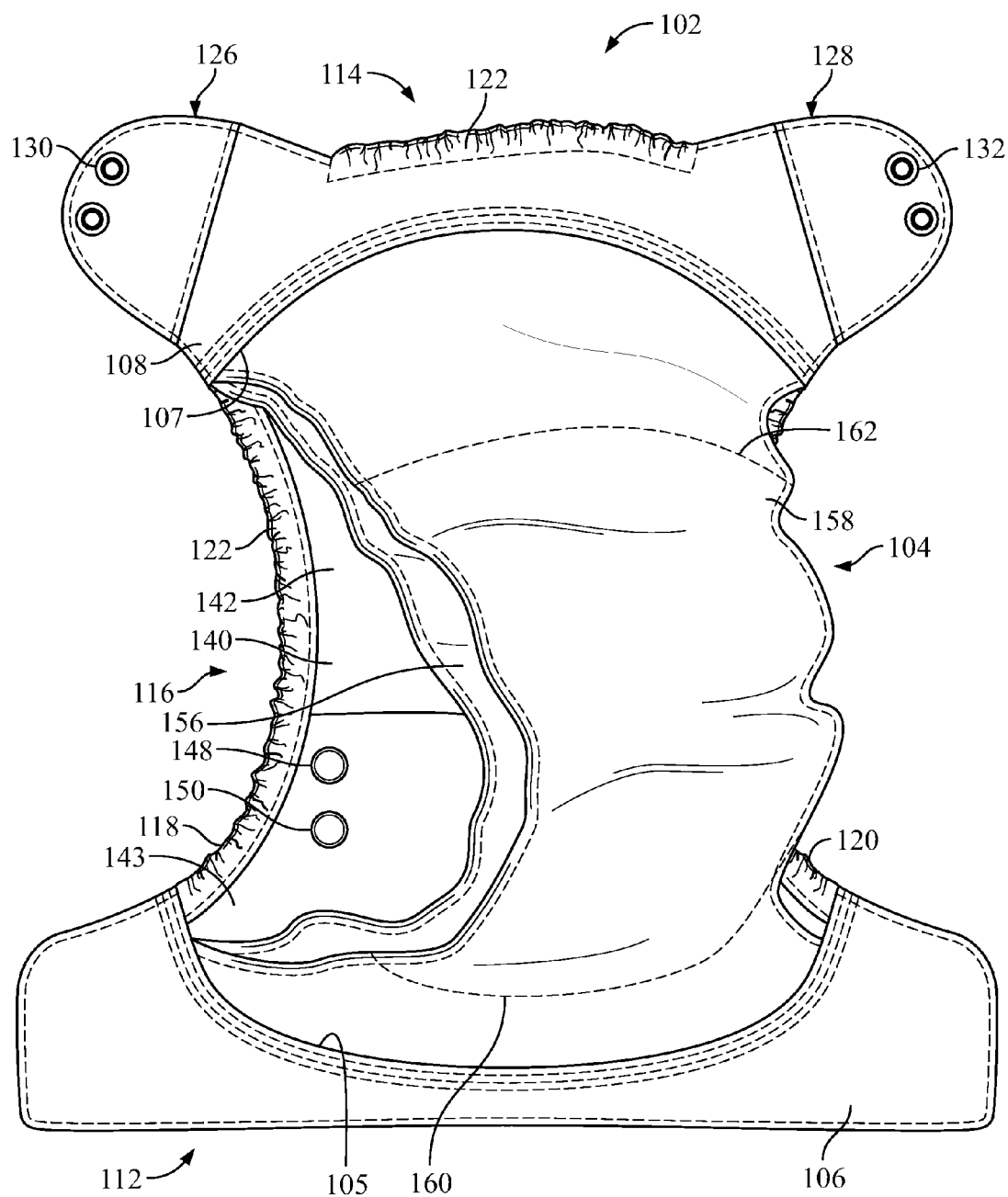
FIG. 6 is an inner perspective view of a second exemplary embodiment of a gender neutral reusable diaper having an adjustable fluid-absorbing insert for use in absorbing fluids within the reusable diaper.
Figure 7:
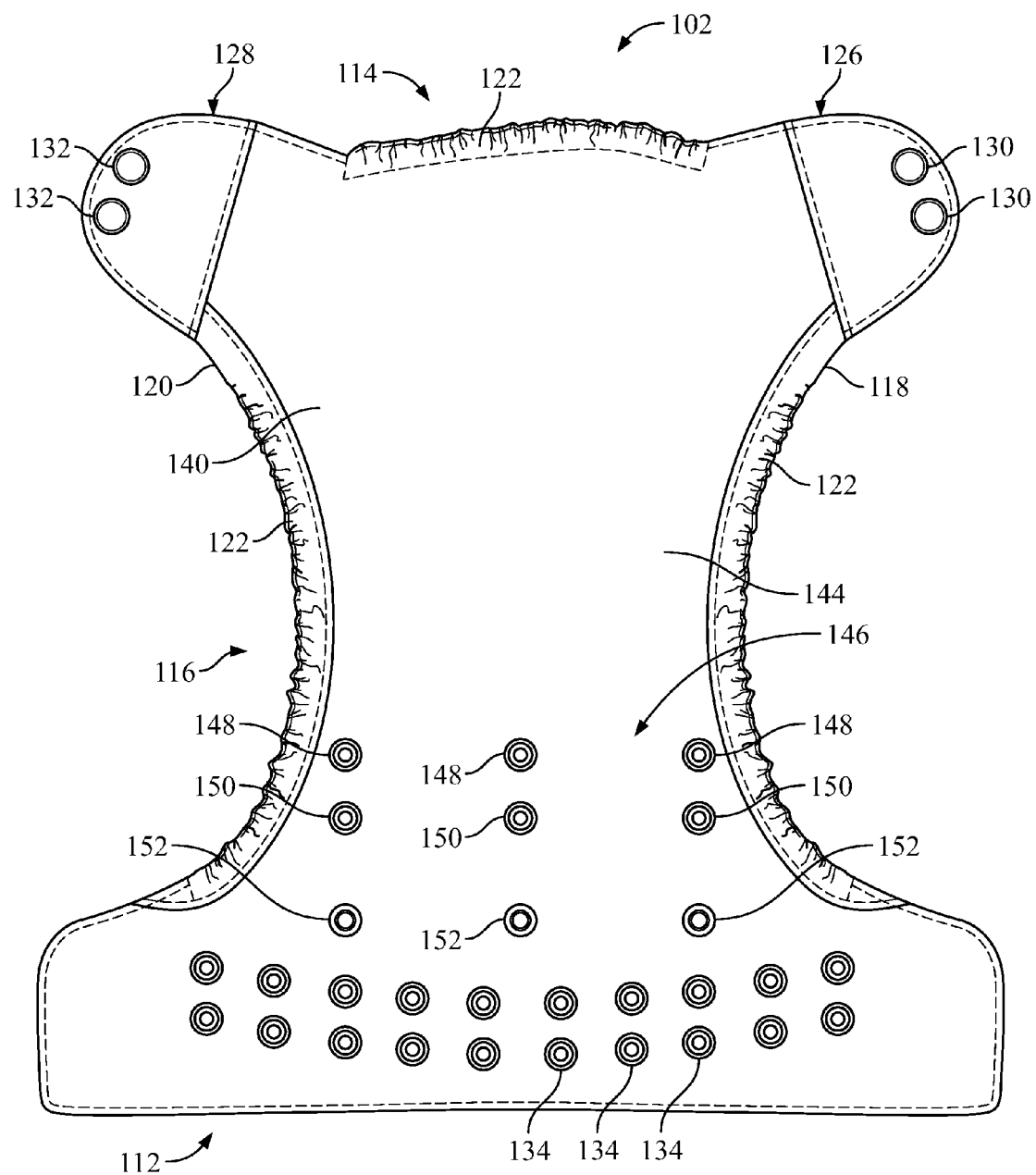
FIG. 7 is an outer view of the reusable diaper shown in FIG. 6.
Figure 8:
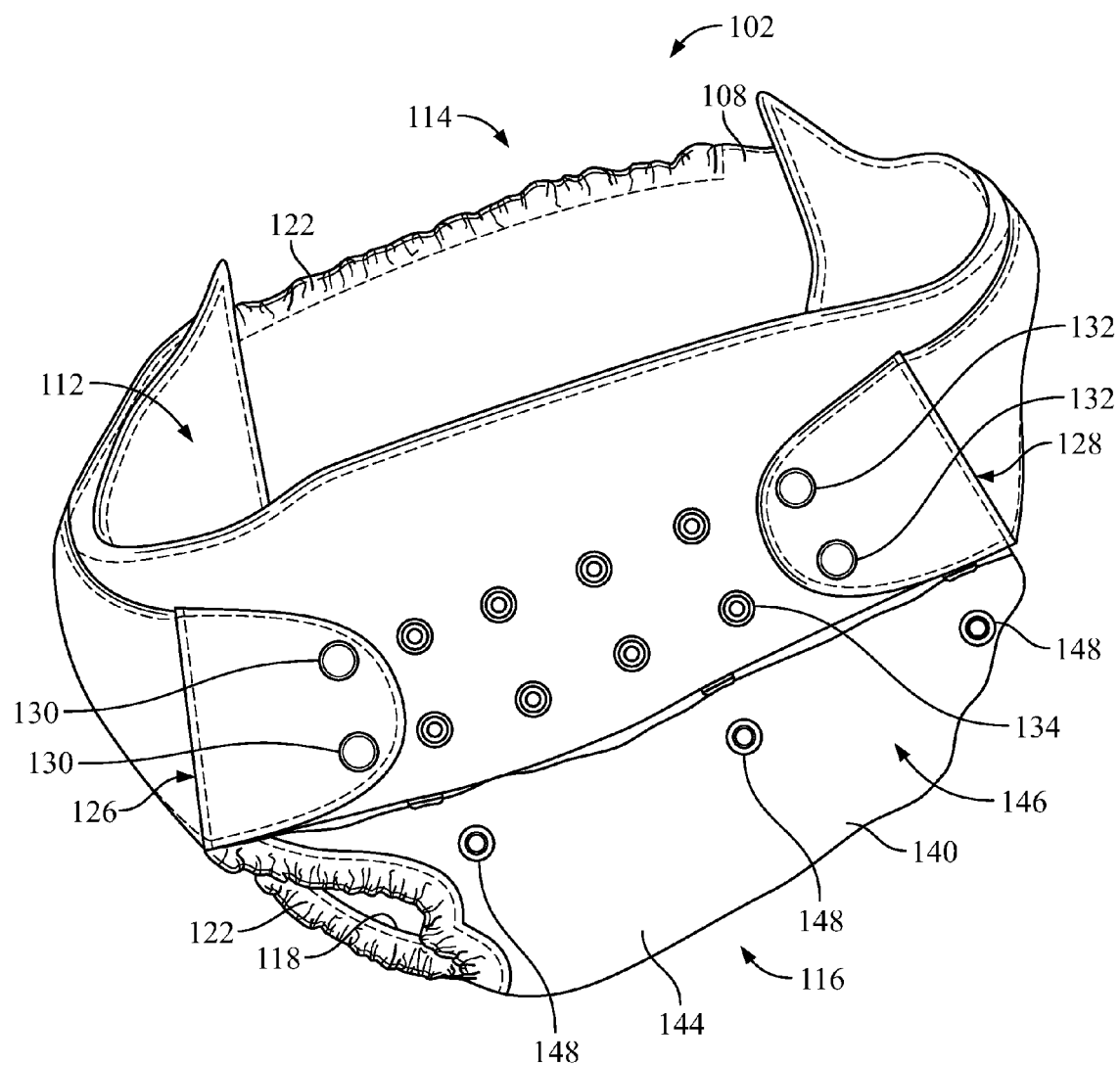
FIG. 8 is a perspective view of the reusable diaper of FIG. 6 shown secured in a generally closed position.

With reference to FIGS. 6-8, the reusable diaper 102 generally includes a forward waist portion 112, a rearward waist portion 114, and a crotch portion 116 disposed generally between the forward and rearward waist portions 112, 114. The contours of the forward and rearward waist portions 112, 114, together with the crotch portion 116, cooperatively define leg openings 118, 120 generally within the crotch portion 116 to accommodate a wearer's legs. In the illustrated embodiment, the leg openings 118, 120 include elastic 122 disposed adjacent the periphery of the leg openings 118, 120 for example, to help draw and hold the reusable diaper 102 securely against the wearer's legs, to inhibit leaking of fluids out of the reusable diaper 102 through the leg openings 118, 120, etc.

The rearward waist portion 114 of the reusable diaper 102 includes corner regions 126, 128 that may be releasably attached to the forward waist portion 112 to secure the reusable diaper 102 in a desired position (e.g., in a generally closed position as shown in FIG. 8, etc.). More particularly, snaps 130, 132 of the respective corner regions 126, 128 may be releasably attached to snaps 134 along the forward waist portion 112 to secure the diaper 102 in the desired position (e.g., in the generally closed position, etc.). As shown in FIG. 6, each corner region 126, 128 includes a pair of spaced-apart male snaps 130, 132, respectively. As shown in FIG. 7, the forward waist portion 112 includes two rows each row having ten female snaps 134. Elastic 122 is disposed along the rearward waist portion 114 to help ensure a snug fit of the reusable diaper 102 around a wearer's waist. Accordingly, this exemplary embodiment of the reusable diaper 102 does not have hook-and-loop fasteners. Alternative embodiments (e.g., reusable diaper 2 (FIGS. 1-5), etc.) may include hook-and-loop fasteners.

The corner regions 126, 128 of the reusable diaper 102 may also be resiliently stretchable. This may allow for at least some adjustability of the diaper's functional waist size as defined by the forward and rearward waist portions 112, 114 when the rearward waist portion 114 is releasably attached to the forward waist portion 112 (e.g., via snaps 130, 132, 134 etc.) in the generally closed position. For example, the corner regions 126, 128 may be formed from about 95% polyester and about 5% Lycra to allow them to stretch. But the corner regions 126, 128 may also be formed from other suitable materials within the scope of the present disclosure, and may or may not be resiliently stretchable.

Having resiliently elastic or stretchable corner regions 126, 128 (and/or elastic 122 along the rearward waist portion 114) with the ability to stretch can allow for tailoring of the diaper's functional waist size to the wearer's actual waist size. For example, the diaper's functional waist size may be selectively tailored for the wearer by stretching the corner regions 126, 128 (and/or elastic 122 along the rearward waist portion 114), and then releasably attaching the snaps 130, 132 to corresponding snaps 134 at desired attachment locations along the forward waist portion 112. In this exemplary manner, the diaper's functional waist size can be selectively adjusted, for example, to provide a relatively snug fit about the waist of the wearer (e.g., infant, toddler, adult, etc.), and preferably without being too uncomfortably tight about the wearer's thighs. While the reusable diaper 102 is described as having snaps, other suitable fasteners for coupling corresponding portions of the reusable diaper 102 together may be used within the scope of the present disclosure, such as hook-and-loop fastener arrangements, adhesives, snaps, buttons, clasps, various hook and loop closures, magnets, combinations thereof, etc.

With continued reference to FIGS. 6-8, the illustrated reusable diaper 102 also generally includes an outer shell 140 that defines or includes an interior or inner surface 142 (FIG. 6) and an exterior or outer surface 144 (FIGS. 7 and 8). The outer shell 140 may be configured to be substantially liquid-impervious and waterproof to thereby resist wicking of moisture through the outer shell 140. In this exemplary embodiment, the outer shell 140 is formed from polyester. Alternatively, the outer shell 140 may be formed from different materials, such as other water resistant materials, coated materials, laminated materials, etc.

With particular reference to FIG. 6, the diaper 102 includes two liquid-resistant regions 106, 108 that, for example, help resist wicking, movement, etc. of moisture through the fluid-absorbent insert 104 past the liquid-resistant regions 106, 108. A forward liquid-resistant region 106 is disposed adjacent the forward waist portion 112. A rearward liquid-resistant region 108 is disposed adjacent the rearward waist portion 114. The forward and rearward liquid-resistant regions 106, 108 each generally include one or more materials, (e.g., layers of material, etc.) that may be coupled (e.g., seamed, stitched, melted, etc.), for example, to the fluid-absorbent insert 104, corner regions 126, 128, and/or outer shell 140.

In this illustrated embodiment, the forward liquid-resistant region 106 is stitched (as shown by the broken lines) to the outer shell 140 and first end portion 105 of the fluid-absorbing insert 104. The rearward liquid-resistant region 108 is stitched (also as shown by the broken lines) to the outer shell 140, second end portion 107 of the fluid-absorbing insert 104, and corner regions 126, 128.

Each liquid-resistant region 106, 108 extends generally across or along the entire width of the respective first and second end portions 105, 107 of the fluid-absorbing insert 104, to resist wicking, movement, etc. of moisture across or through the end portions 105, 107 to the waist portions 112, 114. It should be appreciated that a wide range of suitable materials, coatings, etc. may be used for the liquid-resistant regions 106, 108, including, for example, polyester materials, durable water repellant coatings, laminated fabrics, coated fabrics, etc. For example, the liquid-resistant regions 106, 108 may be formed from the same material, e.g., polyester, as the outer shell 140, although different materials may also be used.

The forward liquid-resistant region 106 may be viewed as defining at least part of the forward waist portion 112. The rearward liquid-resistant region 108 may be viewed as defining at least part of the rearward waist portion 114. Accordingly, the forward liquid-resistant region 106 and the outer shell 140 may broadly be viewed as defining at least part of the forward waist portion 112. And, the forward liquid-resistant region 106, outer shell 140, and corner regions 126, 128 may broadly be viewed as defining at least part of the rearward waist portion 114.

As stated above, the two liquid-resistant regions 106, 108 of the illustrated reusable diaper 102 may help resist wicking, movement, etc. of moisture through the diaper 102 past the liquid-resistant regions 106, 108. In the illustrated embodiment, for example, the forward and rearward liquid-resistant regions 106, 108 are generally disposed adjacent the respective forward and rearward waist portions 112, 114, generally between the waist portions 112, 114 and the fluid-absorbing insert 104. This positioning may help resist wicking, movement, etc. of fluid from the fluid-absorbing insert 104 through the forward and/or rearward waist portions 112 and/or 114 and to a shirt, blanket, article of bedding, etc. that may come into contact with the respective forward and/or rearward waist portions 112 and/or 114 (e.g., with an inner part of the forward and/or rearward waist portions 112 and/or 114, etc.). In other exemplary embodiments, reusable diapers may include one or more inner layers having liquid-resistant regions shaped differently than disclosed herein; having liquid-resistant regions disposed, located, etc. differently than disclosed herein; having liquid-resistant regions with one or more separated parts; having less than or more than two liquid-resistant regions; etc. For example, in one exemplary embodiment, one or more liquid-resistant regions may be disposed adjacent one or more of a forward waist portion, a rearward waist portion, leg regions, etc. of a reusable diaper.

With particular reference now to FIGS. 7 and 8, an adjustment system 146 is provided along the outer surface 144 of the reusable diaper 102 adjacent the forward waist portion 112 to allow for customization or adjustment to the reusable diaper's functional rise and/or crotch length. For example, the adjustment system 146 may allow for adjustment of the reusable diaper 102 such that the reusable diaper 102 may be adjusted to fit different sized wearers. This feature, in combination with the resiliently elastic or stretchable corner regions 126, 128, elastic 122, etc., may provide a generally one-size-fits all reusable diaper 102. This feature may also help create an even better and/or snugger fit to the diaper wearer (e.g., in combination with the resiliently elastic or stretchable corner regions 126, 128, elastic 122, etc.). For example, the adjustment system 146 may help reduce the extent to which the crotch portion 116 hangs down below the wearer. And, the corner region 126, 128 and/or elastic 122 may help securely hold the reusable diaper 102 around a wearer's waist and/or legs. Adjustment systems may be located differently than disclosed herein (e.g., adjacent rearward waist portions, adjacent crotch portions, etc.) within the scope of the present disclosure.

The illustrated adjustment system 146 includes a three-by-three array of snaps 148, 150, 152, horizontally arranged and aligned in three rows and vertically arranged and aligned in three columns. A first row includes three spaced-apart female snaps 148; a second, or middle, row includes three spaced-apart female snaps 150; and a third row includes three-spaced apart male snaps 152. The first row of snap members 148 is vertically spaced from and aligned with the corresponding snap members 150, 152 in the two other rows of the array. Each row of snap members includes a first snap member located generally centrally across a width of the diaper 102, a second snap member located toward one lateral side of the diaper 102, and a third snap member located toward another lateral side of the diaper 102.

The male snaps 152 can be snapped together with either the female snaps 148 of the first row, or the female snaps 150 of the second row. For example, as shown in FIG. 8, the male snaps 152 of the third row can be snapped together with the corresponding female snaps 150 of the second row to thereby decrease the diaper's functional rise and/or crotch length. To decrease the diaper's functional rise and/or crotch length to an even greater extent, the male snaps 152 of the third row may instead be snapped together with the corresponding female snaps 148 of the first row.

The illustrated array of snaps 148, 150, 152 thus provide three different sizing configurations for the reusable diaper 102. The functional rise and/or crotch length of the reusable diaper 102 may be changed by selectively choosing whether to engage the male snaps 152 with the female snaps 148 of the first row, with the female snaps 150 of the second row, or by simply choosing to do neither. Thus, the exemplary three-by-three arrangement can eliminate or at least reduce the bulge in the middle front of the diaper 102 that typically occurs when there are only two columns of snaps due to the fabric bulging out between the two snaps. The three-by-three snap arrangement may help enable the diaper 102 to be more of a one-size fits all diaper 102.

The snaps 148, 150, 152 of the illustrated adjustment system 146 may be formed from a plastic material. Alternatively, the snaps 148, 150, 152 may be formed from other materials, for example lightweight and durable materials that can withstand repeated laundry cycles. In other exemplary embodiments, reusable diapers may include more or less than nine snaps and/or snaps arranged differently than illustrated herein. In addition, reusable diapers may include snaps in other arrangements than disclosed herein, for example, two rows of male snaps with only one row of female snaps, or rows having both male and female snaps. Additional exemplary embodiments include reusable diapers with more or less than three rows of snap members and/or more or less than three columns of snap members.

While the illustrated adjustment system 146 includes an array of snaps 148, 150, 152, other exemplary adjustment systems may be used within the scope of the present disclosure. For example, adjustment systems may include adhesives, buttons, clasps, various hook and loop closures, magnets, elastic straps, adjustable straps, combinations thereof, etc.

The diaper 102 also includes an interior or inner layer 143 configured to serve as a supportive backing for the snaps 134, 148, 150, 152, to thereby help inhibit or keep the snaps from pulling through the outer shell 140. In the illustrated embodiment, the inner layer 142 is stitched to the outer shell 140. The inner layer 143 may be disposed between the outer shell 140 and the end portions 105, 107 of the fluid-absorbing insert 4. The inner layer 143 may also be configured to have a shape matching or corresponding to the forward portion of the diaper 102 (which is the lower portion in FIG. 6). The inner layer 143 may extend between the outer shell 140 and the liquid-resistant region 106.

A wide range of suitable materials may be used for the inner layer 143, including, for example, polyester materials, liquid-resistant materials, liquid-absorbent materials, etc. In an exemplary embodiment, the inner layer 143 comprises a liquid-resistant material such that the diaper 102 includes at least three layers of liquid-resistant material along its forward portion. Alternative embodiments, however, may include an inner layer 143 that is not liquid resistant.

Figure 9:
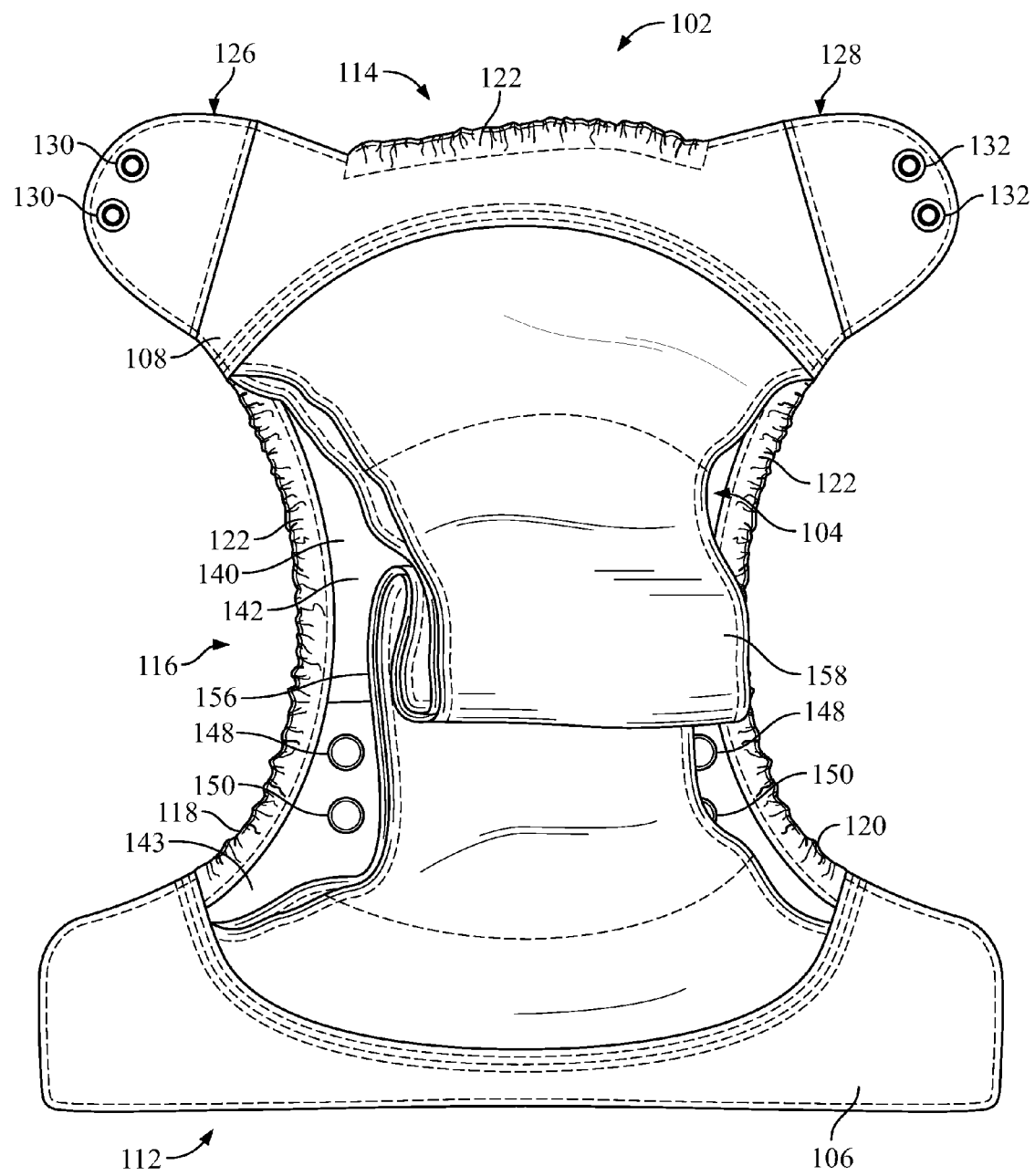
FIG. 9 is a view similar to FIG. 6 with the fluid-absorbing insert shown at least partly folded over itself in position for accommodating use by a female wearer.
Figure 10:
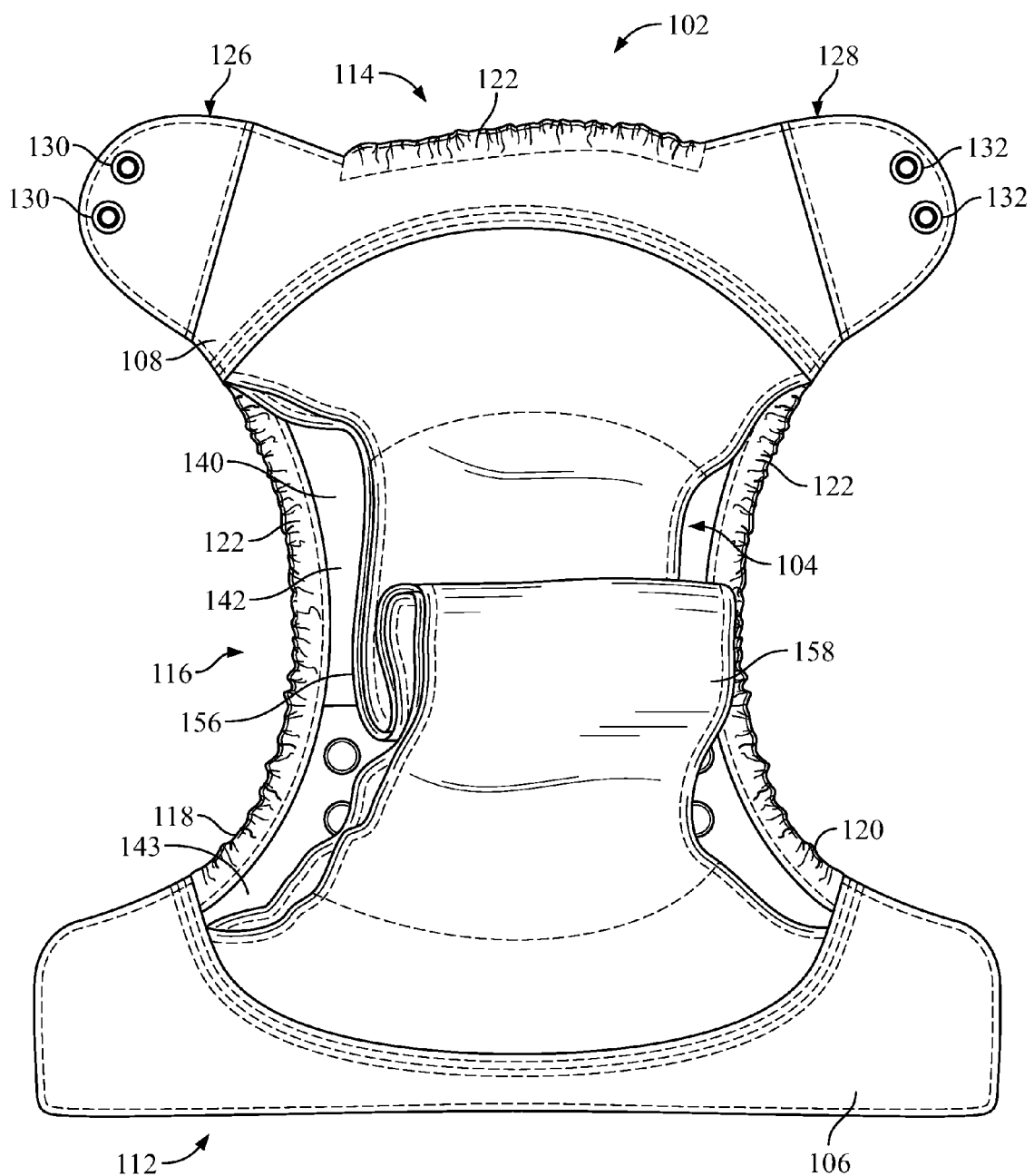
FIG. 10 is a view similar to FIG. 6 with the fluid-absorbing insert shown at least partly folded over itself in position for accommodating use by a male wearer.

With reference now to FIGS. 6, 9, and 10, the adjustable fluid-absorbing insert, pad, or layer 104 of the reusable diaper 102 will be described. The fluid-absorbing insert 104 is positioned within the reusable diaper 102 to absorb liquids within the reusable diaper 102, for example liquids discharged into the reusable diaper 102 by a wearer, etc. In the illustrated embodiment, the fluid-absorbing insert 104 is coupled to the reusable diaper' liquid-resistant regions 106, 108 such that the inner surface 142 of the outer shell 140 is disposed generally between the outer surface 144 of the outer shell 140 and the fluid-absorbing insert 104. In this position, the fluid-absorbing insert 104 may absorb liquids within the reusable diaper 102 (e.g., fluids discharged by the diaper's wearer).

As best shown in FIG. 6, the illustrated fluid-absorbing insert 104 includes two individual and separate (and at least partly spaced apart) first and second layers or pieces of material 156, 158. The second or inner layer or piece of material 158 may absorb liquids within the reusable diaper 102 e.g., fluids discharged by the diaper's wearer). The outer layer 156 may absorb liquids within the reusable diaper 102 that, for example, move outwardly past the inner layer 156, soak through the second or inner layer 156, etc. Wicking of moisture through the second or inner layer 158 to the first or outer layer 156 also helps move that moisture away from being in direct contact with the diaper wearer. Accordingly, the reusable diaper 102 may be put on a wearer with the inner layer 158 positioned against the skin of the wearer. In which case, the inner layer 158 can wick moisture (e.g., bodily discharge, urine, sweat, etc.) through the inner layer 158 to the outer layer 156 of the fluid-absorbent insert 104. At which point, the outer shell 140 inhibits or resists any wicking of moisture through the outer shell 140. Likewise, the liquid-resistant regions 106, 108 inhibit or resists any wicking of moisture through the liquid-resistant regions 106, 108.

The two layers 156, 158 are each stitched (as represented by broken lines) to the reusable diaper's liquid-resistant regions 106, 108 at two locations: a first location (e.g., along the first end portion 105 of the fluid-absorbing insert 104) adjacent the forward waist portion 112 and a second location (e.g., along the second end portion 107 of the fluid-absorbing insert 104) adjacent the rearward waist portion 114. For example, free ends of each of the layers 156, 158 may be overlapped and then stitched to the material forming the liquid-resistant regions 106, 108.

In the illustrated embodiment, the two layers 156, 158 are not further be stitched to each other. Instead, the layers 156, 158 include forward and rearward fold lines 160 and 162 (e.g., stitching, etc.). But in alternative embodiments, the two layers 156, 158 may further be stitched to each other together at third and/or fourth locations adjacent the respective forward and rearward waist portions 112, 114. This may help hold the two layers 156, 158 in position together, and/or may help with sizing and positioning the two layers 156, 158 as desired. In other exemplary embodiments, reusable diapers may include fluid-absorbing inserts having more than or less than two layers of material. In addition, fluid-absorbing insert layers may be coupled together differently and/or may be coupled to reusable diapers differently (e.g., to inner layers of the reusable diapers at locations other than disclosed herein (e.g., adjacent crotch portions, etc.)) within the scope of the present disclosure. Moreover, a single piece of material may be used to form fluid-absorbing insert layers.

The fluid-absorbing insert 104 may be configured to absorb, wick, etc. moisture generally away, for example, from a diaper wearer, and may be formed of, for example, organic cotton, any suitable absorbent material, etc. In one example embodiment, the layers 156, 158 of the fluid-absorbing insert 104 are formed from organic cotton material. But the fluid-absorbing insert layers 156, 158 may comprise in part or in whole one or more of microfibers, hemp, hydrocolloid materials, other suitable absorbent materials, combinations thereof, etc. within the scope of the present disclosure. Materials other than organic materials may also be used.

As shown in FIGS. 9 and 10, the layers 156, 158 of the fluid-absorbing insert 104 are together adjustable relative to the reusable diaper's outer shell 140, for example, for accommodating use of the reusable diaper 102 either by a female wearer (e.g., FIG. 9, etc.) or a male wearer (e.g., FIG. 10, etc.). The fluid-absorbing insert layers 156, 158 are thus also viewed as adjustable relative to the reusable diaper's forward waist portion 112 and rearward waist portion 114, at locations (e.g., along fold lines 160 or 162, etc.) generally between the forward waist portion 112 and rearward waist portion 114. Such adjustability may allow for positioning the layers 156, 158 of the fluid-absorbing insert 104 as desired to ensure that fluids, for example fluids discharged into the reusable diaper 102 by a wearer, are substantially absorbed by the fluid-absorbing insert 104. Thus, this may help inhibit fluids from pooling and/or leaking out of the reusable diaper 102 onto the wearer's clothes, body, bedding, toys, furniture, etc.

To adjust the fluid-absorbing insert 104, the layers 156, 158 are folded (e.g., along fold lines 160 or 162, etc.), bulked up, gathered, etc. over themselves to provide an overlapped, layered, built up, etc. region at the desired location (e.g., at the desired location to accommodate the female or male wearer, etc.). This overlapped region may provide additional liquid absorbing capacity (e.g., additional absorbing material, layers, etc.) at the desired location within the reusable diaper 102, and thus help inhibit undesired leaks. As shown in FIG. 9, for example, the fluid-absorbing insert layers 156, 158 can be folded (e.g., along fold line 162, etc.) over themselves adjacent the reusable diaper's crotch portion 116 and/or rearward portion 114 to accommodate use by a female wearer. Here, the fluid-absorbing insert layers are overlapped at a typical central location to absorb fluids discharged by the female wearer. And as shown in FIG. 9, for example, the fluid-absorbing insert layers 156, 158 can be folded (e.g., along fold line 160, etc.) over themselves adjacent the reusable diaper's forward waist portion 112 to accommodate use by a male wearer. Here, the fluid-absorbing insert layers 156, 158 are overlapped at a typical forward location to absorb fluids discharged by the male wearer.

It should now be appreciated that the reusable diaper 102 may be put on either male or female wearers having varying, differing, etc. body sizes, waist sizes, etc. The adjustment system 146 may first be adjusted to accommodate the body size of the wearer. The reusable diaper 102 may then be put on the wearer with the inner layer 158 of the fluid-absorbing insert 104 (as well as part of the liquid-resistant regions 106, 108) positioned against the skin of the wearer. The fluid-absorbing insert 104 may be folded, bulked up, etc. at the desired location to accommodate a male or female wearer. The snaps 130 and 132 of the first and second corner regions 126, 128 of the rearward waist portion 114 may next be snapped to selected snaps 134 along the forward waist portion 112 to secure the reusable diaper 102 on the wearer. In this position, the fluid-absorbing insert 104 can absorb moisture from the wearer (e.g., bodily discharge, urine, sweat, etc.). When the fluid-absorbing insert 104 becomes saturated, the reusable diaper 102 may be removed from the wearer and washed or laundered. After the reusable diaper 102 (and fluid-absorbing insert 104) has been satisfactorily washed and dried, the reusable diaper 102 may be reused.

In other exemplary embodiments, reusable diapers may include fluid-absorbing inserts releasably coupled to the reusable diapers. For example, snaps, adhesives, buttons, clasps, various hook and loop closures, magnets, elastic straps, adjustable straps, combinations thereof, etc. may be used to couple the fluid-absorbing inserts to the reusable diapers. Here, when the fluid-absorbing inserts become saturated, soiled, etc., they may be washed and/or laundered either together with the reusable diaper or separate therefrom. If laundered separate and after the fluid-absorbing inserts and the reusable diapers are washed and dried, the fluid-absorbing inserts may be repositioned within and re-coupled to the reusable diapers for further use.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom," "side", "inner," "outer," etc. describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order or performance. It is also to be understood that additional or alternative steps may be employed.

The description of the disclosure is merely exemplary in nature and, thus, variations that do not depart from the gist of the disclosure are intended to be within the scope of the disclosure. Such variations are not to be regarded as a departure from the spirit and scope of the disclosure.

What is claimed is:

1. A gender neutral reusable diaper, comprising:
   an outer layer formed of a substantially liquid-impervious material;
   at least one fluid-absorbing insert for use in absorbing fluids;
   a forward waist portion;
   a rearward waist portion; and
   a crotch portion disposed generally between the forward waist portion and the rearward waist portion;
   wherein the at least one fluid-absorbing insert has a first end portion and a second end portion opposite the first end portion, the first end portion is fastened to the diaper at a first location adjacent the forward waist portion, and the second end portion is fastened to the diaper at a second location adjacent the rearward waist portion; and
   wherein the at least one fluid-absorbing insert includes a portion between the first and second end portions that is along and/or defines the crotch portion when not folded over itself and that is adjustable relative to the crotch portion between the first location and the second location for selectively changing an overlapped region of the at least one fluid-absorbing insert to accommodate use by a male and/or a female.

2. The gender neutral reusable diaper of claim 1, wherein the at least one fluid-absorbing insert includes at least two individual and separate layers of material at least partly spaced apart and separate from each other along at least part of longitudinal edge portions of the at least two layers of material.

3. The gender neutral reusable diaper of claim 1, wherein the first and second end portions of the at least one fluid-absorbing insert are fastened to the diaper by stitches adjacent the forward waist portion and adjacent the rearward waist portion, such that the at least one fluid-absorbing insert does not have free ends.

4. The gender neutral reusable diaper of claim 1, wherein the at least one fluid-absorbing insert is adjustable at a desired location between the forward waist portion and the rearward waist portion by folding at least part of the at least one fluid-absorbing insert over itself at the desired location.

5. The gender neutral reusable diaper of claim 1, wherein:
   the at least one fluid-absorbing insert is adjustable for accommodating use by a male by folding at least part of the at least one fluid-absorbing insert over itself adjacent the forward waist portion; and/or
   the at least one fluid-absorbing insert is adjustable for accommodating use by a female by folding at least part of the at least one fluid-absorbing insert over itself adjacent the crotch portion.

6. The gender neutral reusable diaper of claim 1, further comprising an adjustment system adjacent the forward waist portion, the adjustment system allowing adjustment of the reusable diaper to fit different sized wearers.

7. The gender neutral reusable diaper of claim 6, wherein the adjustment system includes a three-by-three array of snaps along the outer layer of the reusable diaper that allows selective adjustment to a functional rise of the reusable diaper, the array of snaps including at least a first row of three spaced-apart snaps vertically spaced from and aligned with corresponding snaps in two other rows of the array, and wherein the first row of snap members include a first snap member located generally centrally across a width of the diaper, a second snap member located toward one lateral side of the diaper, and a third snap member located toward another lateral side of the diaper.

8. The gender neutral reusable diaper of claim 1, wherein the at least one fluid-absorbing insert is at least partially formed from organic material.

9. The gender neutral reusable diaper of claim 1, further comprising at least one liquid-resistant region oriented for resisting wicking of moisture from the at least one fluid-absorbing insert past the at least one liquid-resistant region to a waist edge portion of the diaper.

10. The gender neutral reusable diaper of claim 1, further comprising:
a first liquid-resistant region located adjacent the forward waist portion; and
a second liquid-resistant region being located adjacent the rearward waist portion.

11. The gender neutral reusable diaper of claim 10, wherein the first and second end portions of the at least one fluid-absorbing insert are fastened to the respective first and second liquid-resistant regions.

12. The gender neutral reusable diaper of claim 11, wherein:
the first and second end portions of the at least one fluid-absorbing insert are fastened by stitches to the respective first and second liquid-resistant regions, such that the at least one fluid-absorbing insert does not have free ends;
the portion of the at least one fluid-absorbing insert between the first and second end portion is not directly attached to the diaper;
the first liquid-resistant region is operable for resisting wicking of moisture from the first end portion of the at least one fluid-absorbing insert past the first liquid-resistant region to the forward waist edge portion; and
the second liquid-resistant region is operable for resisting wicking of moisture from the second end portion of the at least one fluid-absorbing insert past the second liquid-resistant region to the rearward waist edge portion.

13. The gender neutral reusable diaper of claim 1, wherein the rearward waist portion has at least one resiliently stretchable corner region for use in securing the diaper in a desired position.

14. A gender neutral reusable diaper, comprising:
an outer shell formed of a substantially liquid-impervious material;
a forward waist portion defining a forward waist edge portion of the diaper
a rearward waist portion defining a rearward waist edge portion of the diaper;
a crotch portion disposed generally between the forward waist portion and the rearward waist portion;
a first liquid-resistant region located adjacent the forward waist portion;
a second liquid-resistant region located adjacent the rearward waist portion;
at least one fluid-absorbing layer for use in absorbing fluids, the at least one fluid-absorbing layer having a first end portion fastened to the first liquid-resistant region at a first location and a second end portion fastened to the second liquid-resistant region at a second location, such that the at least one fluid-absorbing layer does not have any free ends;
wherein:
the first liquid-resistant region is between the forward waist edge portion of the diaper and the at least one fluid-absorbing layer for resisting movement of fluid from the first end portion of the at least one fluid-absorbing layer along the forward waist portion to the forward waist edge portion;
the second liquid-resistant region is between the rearward waist edge portion of the diaper and the at least one fluid-absorbing layer for resisting movement of fluid from the second end portion of the at least one fluid-absorbing layer along the rearward waist portion to the rearward waist edge portion; and
the at least one fluid-absorbing layer includes a portion between the first and second end portions that is adjustable relative to the crotch portion between the first and second locations of the at least one fluid-absorbing layer for selectively changing an overlapped region of the at least one fluid-absorbing layer to accommodate use by a male and/or a female.

15. The gender neutral reusable diaper of claim 14, wherein the at least one fluid-absorbing layer includes at least two individual and separate layers of material at least partly spaced apart and separate from each other along at least part of longitudinal edge portions of the at least two layers of material.

16. The gender neutral reusable diaper of claim 14, wherein the at least one fluid-absorbing layer is adjustable at a desired location between the forward waist portion and the rearward waist portion by folding at least part of the at least one fluid-absorbing layer over itself at the desired location.

17. The gender neutral reusable diaper of claim 14, wherein:
the at least one fluid-absorbing layer is adjustable for accommodating use by a male by folding at least part of the at least one fluid-absorbing layer over itself adjacent the forward waist portion; and/or
the at least one fluid-absorbing layer is adjustable for accommodating use by a female by folding at least part of the at least one fluid-absorbing layer over itself adjacent the crotch portion.

18. The gender neutral reusable diaper of claim 14, wherein the at least one fluid-absorbing layer is at least partially formed from organic material.

19. The gender neutral reusable diaper of claim 14, wherein:
the first and second end portions of the at least one fluid-absorbing layer are fastened by stitches to the respective first and second liquid-resistant regions, such that the at least one fluid-absorbing layer does not have free ends; and
the portion of the at least one fluid-absorbing layer between the first and second end portion is not directly attached to the diaper.

20. A gender neutral reusable diaper, comprising:
an outer layer formed of a substantially liquid-impervious material;
a forward waist portion;
a rearward waist portion opposite the forward waist portion;
a crotch portion between the forward waist portion and the rearward waist portion;
at least one fluid-absorbing insert having a first end portion, a second end portion opposite the first end portion, and a portion between the first and second end portions;
wherein:
the forward waist portion, the rearward waist portion and the crotch portion cooperatively define leg openings to accommodate a wearer's legs when the gender neutral diaper is configured for use;

the first end portion of the at least one fluid-absorbing insert is attached to the diaper at a first location closer to the forward waist portion than the rearward waist portion;

the second end portion of the at least one fluid-absorbing insert is attached to the diaper at a second location closer to the rearward waist portion than the forward waist portion; and the portion of the at least one fluid-absorbing insert between the first and second end portions is along and/or defines the crotch portion when not folded over itself and is selectively overlappable therefrom to create an overlapped region of the at least one fluid-absorbing insert at a selectable position between the first and second locations to accommodate use by a male when the overlapped region is positioned at a forward location adjacent the forward waist portion for absorbing fluids discharged by the male wearer or to accommodate use by a female when the overlapped region is positioned at a central location for absorbing fluids discharged by the female wearer.

21. The gender neutral reusable diaper of claim 20, wherein:

each of the forward waist portion and the rearward waist portion includes a liquid resistant region to resist movement of moisture from the crotch portion through the forward and rearward waist portions;

the rearward waist portion has two resiliently stretchable corner regions releasably attachable to the forward waist portion for securing the diaper in a desired position;

the diaper further comprises an adjustment system on the outer layer of the diaper for adjusting a crotch length of the diaper;

the portion of the at least one fluid-absorbing insert between the first and second end portion is not directly attached to the diaper; and the first and second end portions of the at least one fluid-absorbing insert are attached by stitching at the respective first and second locations, such that the at least one fluid-absorbing insert does not have free ends.

\* \* \* \* \*